US005756095A

United States Patent [19]
Jutila

[11] Patent Number: 5,756,095
[45] Date of Patent: May 26, 1998

[54] ANTIBODIES WITH SPECIFICITY FOR A COMMON EPITOPE ON E-SELECTIN AND L-SELECTIN

[75] Inventor: Mark A. Jutila, Bozeman, Mont.

[73] Assignee: The Research and Development Institute, Inc., Bozeman, Mont.

[21] Appl. No.: 463,707

[22] Filed: Jun. 5, 1995

Related U.S. Application Data

[63] Continuation of Ser. No. 64,505, May 19, 1993, abandoned, which is a continuation-in-part of Ser. No. 887,695, May 22, 1992, abandoned.

[51] Int. Cl.$^6$ .................. A61K 39/395; C07K 16/28; G01N 33/53
[52] U.S. Cl. ......................... 424/144.1; 424/143.1; 424/152.1; 424/153.1; 424/154.1; 424/172.1; 424/173.1; 435/7.1; 435/7.2; 435/7.11; 435/7.24; 435/70.21; 435/172.2; 530/388.2; 530/388.22; 530/388.73; 530/388.75; 530/389.6
[58] Field of Search ............... 424/130.1, 133.1, 424/141.1, 143.1, 144.1, 152.1, 153.1, 154.1, 172.1, 173.1; 435/70.21, 172.2, 240.27, 7.21, 7.24, 326, 328, 334, 343, 343.1, 343.2, 7.1, 7.2; 530/387.1, 387.3, 388.1, 388.22, 388.7, 388.73, 388.75, 389.1, 389.6

[56] References Cited

U.S. PATENT DOCUMENTS

| | | | |
|---|---|---|---|
| 4,849,509 | 7/1989 | Thurin et al. | 530/387 |
| 4,935,234 | 6/1990 | Todd, III et al. | 424/85 |
| 5,002,873 | 3/1991 | St. John et al. | 435/69.1 |
| 5,011,778 | 4/1991 | Newman et al. | 435/240.27 |
| 5,019,648 | 5/1991 | Schlossman et al. | 530/387 |
| 5,039,793 | 8/1991 | Bernard et al. | 530/350 |
| 5,071,964 | 12/1991 | Dustin et al. | 530/395 |
| 5,080,883 | 1/1992 | Lyle et al. | 424/1.1 |
| 5,081,034 | 1/1992 | Bevilacqua et al. | 435/252.33 |
| 5,098,833 | 3/1992 | Lasky et al. | 435/69.1 |

OTHER PUBLICATIONS

Waldmann Science 252: 1657–1662 (1991).
Shaffer Biotechnology New Swatch Oct. 4, 1993 p. 9.
Jolliffe Intern. Rev. Immunology 10:241–250 (1993).
Bargatze et al. J. Immunology 152:5814–5825 (1994).
J. Mountain et al. Biotech Gen. Eng. Rev. 10: 1, 10–13 only 1992.
Harris et al. Tbtech 11:42–45 (1993).
Antman et al. Circulation 81:1744–1752 (1990).
Johnson et al. JACC 13:27–35 (1989).
Coller et al. J. Clin Invest. 72: 325–338 (1983).
Coller et al. Blood 66: 1456–1459 (1985).
Kahn et al. J. Cell Biol. 125:461–470 (1994).
Walcheck et al. J. Exp. Med. 178:853–863 (1993).
Steinberg et al. J. Heart Lung Transplant 13:306–318 (1994).
Picker, Louis J.; Kishimoto, Takashi K.; Smith, C. Wayne; Warnock, R. Aaron; and Butcher, Eugene C.; "ELAM–1 Is An Adhesion Molecule For Skin–Homing T Cells", Nature, Vo. 349, pp 796–799 (Feb 28, 1991).

Shimizu, Yoji; Shaw, Stephen; Graber, Norma; Gopal, T. Venkat; Horgan, Kevin J.; Van Seventer, Gijs A.; and Newman, Walter: "Activation–Independent Binding Of Human Memory T Cells to Adhesion Molecule ELAM–1", Nature, vol. 349, pp. 799–802 (Feb. 28, 1991).

Bevilacqua, Michael P.; Stengelin, Siegfried; Gimbrone, Jr., Michael A.; and Seed, Brian: "Endothelial Leukocyte Adhesion Molecule 1; An nducible Receptor For Neutrophils Related to Complement Regulatory Proteins And Lectins", Science, vol. 243, pp. 1160–1165 (Mar. 3, 1989).

Edgington, Stephen M.: "How Sweet It Is: Selectin–Mediating Drugs", Bio–Technology, vol. 10 (Apr. 1992).

Geng, Jian–Guo; Bevilacqua, Micahel P.; Moore, Kevin L.; McIntyre, Thomas M.; Prescott, Stephen M.; Kim, Jenny M.; Bliss, Greg A.; Zimmerman, Guy A.; and McEver Rodger P.: "Rapid Neutrophil Adhesion To Activated Endothelium Mediated By GMP–140", Nature, vol. 343, pp. 757–760 (Feb. 22, 1990).

Picker, Louis J.; Warnock, R. Aaron; Burns, Alan R.; Doerschuk, Claire M.; Berg, Ellen L.; and Butcher, Eugene C.: "The Neutrophil Selectin LECAM–1 Presents Carbohydrate Ligands To The Vascular Selectins ELAM–1 and GMP–140", Cell, vol. 66, pp. 921–933 (Sep. 6, 1991).

Larsen, Eric; Celi, Alessandro; Gilbert, Gary E.; Furie, Barbara C.; Erban, John K.; Bonfanti, Roberta; Wagner, Denisa D.; and Furie, Bruce: "PADGEM Protein: A Receptor That Mediates The Interaction Of Activated Platelets With Neutrophils And Monocytes", Cell, vol. 59, pp. 305–312 (Oct. 20, 1989).

Johnston, Geoffrey I.; Cook, Richard G.; and McEver, Rodger P.: "Cloning of GMP–140, A Granule Membrane Protein Of Platelets And Endothelium: Sequence Similarity To Proteins Involved In Cell Adhesion And Inflammation", Cell, vol. 56, pp. 1033–1044 (Mar. 24, 1989).

(List continued on next page.)

Primary Examiner—Lila Feisee
Assistant Examiner—Phillip Gambel
Attorney, Agent, or Firm—Morgan & Finnegan, L.L.P.

[57] ABSTRACT

The present invention involves monoclonal antibodies which recognize a common determinant found on separate and distinct adhesion molecules. The monoclonal antibodies are used for blocking cellular adhesion. Monoclonal antibodies are also described that are capable of binding to a common determinant expressed on separate and distinct selectins and in particular antibodies that bind to both E-selectin (also known as ELAM-1) and L-selectin (also known as LAM-I, LECAM-1, Leu-8, TQ-1, gp 90 MEL-14 and peripheral lymph node homing receptor). The monoclonal antibodies are useful in the diagnosis, treatment and prevention of diseases associated with inflammation. The monoclonal antibodies are used for detecting cells bearing selectins. Cell lines capable of producing the above described antibodies are also described.

34 Claims, 23 Drawing Sheets

OTHER PUBLICATIONS

Watson, Susan R.; Imai, Yasuyuki; Fennie, Christopher; Geoffrey, Joyce; Singer, Mark; Rosen, Steven D.; and Lasky, Laurence A.: "The Complement Binding–Like Domains Of The Murine Homing Receptior Facilitate Lectin Activity", *The Journal of Cell Biology*, vol. 115, No. 1, pp. 235–243 (Oct. 1991).

Pigott, Rod; Needham, Lindsey A.; Edwards, R. Mark; Walker, Caroline; and Power, Christine: "Structural And Functional Studies Of The Endothelial Activation Antigen Endothelial Leucocyte Adhesion Molecule–1 Using a Panel Of Monoclonal Antibodies", *The Journal Of Immunology*, Vo. 147, No. 1, pp., 130–135 (Jul. 1, 1991).

Berg, Ellen Lakey; Goldstein Leslie A.; Jutila, Mark A.; Nakache, Maurice; Picker, Louis J.; Streeter, Philip R.; Wu, Nora W.; Zhou, David; and Butcher, Eugene C.: "Homing Receptors and Vascular Addressins: Cell Adhesion Molecules That Direct Lymphocyte Traffic", *Immunological Reviews*, No. 108, pp. 5–18 (1989).

Spertini, Olivier; Luscinskas, Francis W.; Kansas, Geoffrey S.; Munro, J. Michael; Griffin, James D.; Gimbrone, Jr., Michael A.; and Tedder, Thomas F.: "Leukocyte Adhesion Molecule–1 (LAM–1, L–Selectin) Interacts With An Inducible Endothelial Cell Ligand To Support Leukocyte Adhesion", *The Journal Of Immunology*, vol. 147, No. 8, pp. 2565–2573 (Oct. 16, 1991).

Berg, Ellen L.; Robinson, Martyn K.; Warnock, R. Aairon; and Butcher, Eugene C.: "The Human Peripheral Lymph Node Vascular Addressin Is A Ligand For LECAM–1, The Peripheral Lymph Node Homing Receptor", *The Journal of Cell Biology*, vol. 114, No. 2, pp. 343–349 (Jul. 1991).

Bevilacqua, Michael P.; Pober, Jordan S.; Mendrick, Donna L.; Cotran, Ramzi S.; and Gimbrone, Jr., Michael A.: "Identification Of An Inducible Endothelial–Leukocyte Adhesion Molecule (Inflammation/Cytokine/Endotoxin/Neutrophil/HL–60 Cell)", *Proc. Natl. Acad. Sci. USA*, vol. 84, pp. 9238–9242 (Dec. 1987).

Mulligan, Michael S.; Varani, James; Dame, Michael K.; Lane, Caryl L.; Smith, C. Wayne; Anderson, Donald C.; and Ward, Peter A.: "Role of Endothelial–Leukocyte Adhesion Molecule 1 (ELAM–1) In Neutrophil–Mediated Lung Injury In Rats", *J. Clin. Invest.*, vol. 88, pp. 1396–1406 (Oct. 1991).

Jutila, Mark A.; Rott, Lusijah; Berg, Ellen L.; and Butcher, Eugene C.: "Function and Regulation Of The Neutrophil MEL–14 Antigen In Vivo: Comparison With LFA–1 And MAC–1", *The Journal Of Immunology*, vol. 143, No. 10, pp. 3318–3324 (Nov. 15, 1989).

Kishimoto, Takashi Kei; Jutila, Mark A.; Berg, Ellen Lakey; and Butcher, Eugene C.: "Neutrophil Mac–1 and MEL–14 Adhesion Proteins Inversely Regulated By Chemotactic Factors", *Science*, vol. 245, pp. 1238–1241 (Sep. 15, 1989).

Dunlop, Lindsay C.;l Skinner, Michael P.; Bendall, Linda J.; Favaloro, Emmanuel J.; Castaldi, Peter A.; Gorman, Jeffrey J.; Gamble, Jennifer R.; Vadas, Matthew A.; and Berndt, Michael C.: "Characterization of GMP–140 (P–selectin) as a Circulating Plasma Protein", *J. Exp. Med.*, The Rockefeller University Press, vol. 175, pp. 1147–1150 (Apr. 1992).

Rothlein, Robert; Mainolfi, Elizabeth A.; Czajkowski, Michele; and Marlin, Steven D.: "A Form Of Circulating ICAM–1 In Human Serum", *The Journal Of Immunology*, vol. 147, No. 11, pp. 3788–3793 (Dec. 1, 1991).

Von Adrian, Ulrich H.; Chambers, J. David; McEvoy, Leslie M.; Bargatze, Robert F.; Arfors, Karl E.; and Butcher, Eugene C.: "Two–Step Model Of Leukocyte–Endothelial Cell Interaction In Inflammation: Distinct Roles For LECAM–1 And The Leukocyte B2 Integrins In Vivo", *Proc. Natl. Acad. Sci. USA*, vol. 88, pp. 7538–7542 (Sep. 1991).

Ley, Klaus; Gaehtgens, Peter; Fennie, Christopher; Singer, Mark S.; Lasky, Laurence A.; and Rosen, Steven D.: "Lectin–Like Cell Adhesion Molecule 1 Mediates Leukocyte Rolling In Mesenteric Venules In Vivo", *Blood*, vol. 77, No. 12, pp. 2553–2555 (Jun. 15, 1991).

Smith, C. Wayne; Kishimoto, Takashi Kei; Abbas, Omid; Hughes, Bonnie; Rothlein, Robert; McIntire, Larry V.; Butcher, Eugene; and Anderson, Donald C.: "Chemotactic Factors Regulate Lectin Adhesion Molecule 1 (LECAM–1)–Dependent Neutrophil Adhesion To Cytokine–Stimulated Endothelial Cells In Vitro", *J. Clin Invest.*, vol. 87, pp. 609–618 (Feb. 1991).

Watson, Susan R.; Fennie, Christopher; and Lasky, Laurence A.: "Neutrophil Influx Into An Inflammatory Site Inhibited By A Soluble Homing Receptor –IgG Chimaera" *Nature*, vol. 349, pp 164–167 (Jan. 10, 1991).

Lewinsohn, David M.; Bargatze, Robert F.; and Butcher, Eugene C.: "Leukocyte–Endothelial Cell Recognition: Evidence Of A Common Molecular Mechanism Shared By Neutrophils, Lymphocytes, And Other Leukocytes", *The Journal Of Immunology*, vol. 138, No. 12, pp. 4313–4321 (Jun. 15, 1987).

Isobe, Mitsuaki; Yagita, Hideo; Okumura, Ko; and Ihara, Akira: "Specific Acceptance Of Cardiac Allograft After Treatment With Antibodies To ICAM–1 and LFA–1", *Science*, vol. 255, pp. 1125–1127 (Feb. 28, 1992).

Gundel, Robert H.; Wegner, Craig D.; Torcellini, Carol A.; Clarke, Cosmos C.; Haynes, Nancy; Rothlein, Robert; Smith, C. Wayne; and Letts, L. Gordon: "Endothelial Leukocyte Adhesion Molecule–1 Mediates Antigen–Induced Acute Airway Inflammation And Late–Phase Airway Obstruction In Monkeys", *J. Clin. Invest.* vol. 88, pp. 1407–1411 (Oct. 1991).

Kishimoto, Takashi Kei: "A Dynamic Model For Neutrophil Localization to Inflammatory Sites", *The Journal of NIH Research*, vol. 3, pp. 75–77 (Sep. 1991).

Hallmann, R.; Jutila, M.A.; Smith, C.W.; Anderson, D.C.; Kishimoto, T.K.; and Butchr, E.C.: "The Peripheral Lymph Node Homing Receptor, LECAM–1, Is Involved in CD18–Independent Adhesion Of Human Neutrophils To Endothelium", *Biochemical And Biophysical Research Communications*, vo. 174, No. 1, pp. 236–243 (Jan. 15, 1991).

Kishimoto, Takashi Kei; Warnock, R. Aaron; Jutila, Mark A.; Butcher, Eugene C.; Lane, Carol; Anderson, Donald C.; and Smith, C. Wayne: "Antibodies Against Human Neutrophil LECAM–1 (LAM–1/Leu–8/DREG–56 Antigen) and Endothelial Cell ELAM–1 Inhibit A Common CD18–Independent Adhesion Pathway In Vitro", *Blood*, vol. 78, No. 3, pp. 805–811 (Aug. 1991).

Smith, C. Wayne; Kishimoto, Takashi Kei; Abbass, Omid; Hughes, Bonnie; Rothlein, Robert; McIntire, Larry V.; Butcher, Eugene; and Anderson, Donald C.: "Chemotactic Factors Regulate Lectin Adhesion Molecule 1 (LECAM 1)–Dependent Neutrophil Adhesion To Cytokine–Stimulated Endothelial Cells In Vitro", *J. Clin. Invest.*, vol. 87, pp. 609–618 (Feb. 1991).

Sigma Chemical Co. Bio Chemicals Catalog, p. 1135, #F7387 and F1640 (1991).

Pierschbacher et al., *Cell* 26:259–(1981).
Alberts et al. (1989) "Molecular Biology of the Cell", *Garland Publishing, Inc.*, New York, pp. 816–818.
Waldeman, T.A., (1991) *Science* 252:1657–1622.
Harlow et al. "Antibodies: A Laboratory Manual", Cold Spring Harbor Pub., Cold Spring Harbor, NY pp. 72–77, 92–97, 128–135 and 141–157.

Kishimoto et al. (1990) *Proc. Natl. Acad. Sci.* 87:2244–2248.
Lasky (1992) *Science* 258:964–969.
Jutila et al. Characterization of a Functionally Important and Evolutionarily Well–conserved Epitope Mapped to the Short Consensus Repeats of E–Selectin and L–Selectin. (Jun. 1992) *J. Exp. Med.* 175:1565–1573.

Before Array

Log 10 fluorescence ⟶

After Array

Log 10 fluorescence ⟶

After Array

Log 10 fluorescence ⟶

BLOOD

FITC-labed
Transferred Lymphocytes

SPLEEN

FITC-labed
Transferred Lymphocytes

PLN

FITC-labed
Transferred Lymphocytes

BLOOD

FITC-labed
Transferred Lymphocytes

SPLEEN

FITC-labed
Transferred Lymphocytes

PLN

FITC-labed
Transferred Lymphocytes

ANTIBODIES WITH SPECIFICITY FOR A COMMON EPITOPE ON E-SELECTIN AND L-SELECTIN

CROSS REFERENCE TO RELATED APPLICATION

This is a continuation of application Ser. No. 08/064,505, filed on May 19, 1993, now abandoned, which is a CIP of Ser. No. 07/887/695 filed May 22, 1992 now abandoned.

FIELD OF INVENTION

This invention relates to antibodies that bind to multiple adhesion molecules and methods for treatment of diseases. Another aspect of the invention relates to immunoassays for detection of adhesion molecules.

BACKGROUND OF THE INVENTION

Peripheral blood in the circulatory system of humans and mammals is comprised principally of red blood cells, i.e. erythrocytes, and white blood cells, i.e. leukocytes. The family of white blood cells is comprised of monocytes, neutrophils, eosinophils, basophils and various types of lymphocytes. Neutrophils, eosinophils and basophils are known as "granulocytes" because of their content of cytoplasmic granules.

Neutrophils, monocytes, eosinophils and basophils are known as phagocytes because their primary function in the human immune system is to phagocytize or ingest bacteria, microorganisms and other types of foreign materials. These cells are produced from common progenitor cells in the bone marrow of a human or animal and are known to circulate in peripheral blood and finally, enter tissues as necessary for control of infection or to participate in inflammatory reactions. However, each of the phagocytes has different functions and behaves as a related but separate system.

The neutrophil is the most common leukocyte in human and animal peripheral blood. One microliter of normal human whole blood contains, on average 5,000 leukocytes of which 3,075 are neutrophils, 150 are eosinophils, 25 are basophils, 250 are monocytes, and 1,500 are lymphocytes.

In the response to infection or inflammation, most leukocytes are activated first to migrate to the appropriate area in response to chemo-attractant factors such as certain bacterial products, complement component, cytokines, and other factors. In addition to leukocytes, these signals can also activate endothelial cells. As a result of activation, leukocytes and endothelial cells become adhesive.

This attraction process is termed "chemotaxis". Once in an area of inflammation or infection, most leukocytes must establish a firm attachment to their targets. Cell adhesion is mediated through various ligand-receptor interactions. Examples include cell receptors for complement; cell receptors for the Fc or cell binding portion of antibodies; fibronectin receptors and other adhesion molecules. Most of the receptors associated with adhesion are glycoproteins.

Neutrophils primarily interact with and exit the arterial-venous system (i.e., extravasate) through the endothelium of postcapillary venules. During an acute inflammatory response, neutrophils are capable of exiting high endothelial venules (HEV) found within lymph nodes, a principal site of lymphocyte extravasation. Two classes of neutrophil surface antigens have been shown to be involved in this interaction—the LFA-1/Mac-1/p150.95 (CD11a–c/CD18) complex and L-selectin.

Selectins, previously called LEC-CAMs, represent a new family of adhesion proteins which regulate leukocyte entry into lymphoid tissues and sites of inflammation (Rosen, 1990 Am. J. Respir. Cell. Mol. Biol., 3:397–402). Three members of this family have been identified. Two of these, E-selectin and P-selectin (originally termed ELAM-1 and GMP-140/PADGEM, respectively), are expressed by endothelial cells. The third, L-selectin (also known as LAM-1, LECAM-1, Leu-8, TQ-1, or peripheral lymph node homing receptor), is expressed by virtually all peripheral blood leukocytes. P-selectin is a cytoplasmic glycoprotein in endothelial cells and platelets which can be rapidly (within minutes) translocated to the cell surface upon activation with thrombin (Larsen et al., 1989 Cell 3:397–402; Johnston et al., 1989 Cell 56:1033–1044; Geng et al., 1990 Nature (London) 343:757–760). E-selectin is also an inducible endothelial cell surface glycoprotein, but requires 2–4 hours for expression, reflecting the requirements for de novo RNA and protein synthesis (Bevilacqua et al., 1989 Proc. Natl. Acad. Sci. USA 84:9238–9242; Bevilacqua et al., 1989 Science (Wash. D.C.) 243:116–1112).

Both P-selectin and E-selectin are adhesion proteins for neutrophils and monocytes (Larsen et al., 1989 Cell 59:305–312; Johnston et al., 1989 Cell 56:1033–1044; Bevilacqua et al., 1987 Proc. Natl. Acad. Sci. 84:9238–9242; Bevilacqua et al., 1989 Science (Wash. D.C.) 243:1160–1112). A subpopulation of memory T-cells has also been shown to bind E-selectin (Picker et al., 1991 Nature (London) 349:796–799); (Shimizu et al., 1991 Nature (London) 349:799). In contrast to vascular selectins, L-selectin is constitutively expressed by leukocytes and mediates lymphocyte adhesion to peripheral lymph node high endothelial venules (HEV) by binding the peripheral vascular addressing (Berg et al., 1989 Immunol. Rev. 108:5–18; Berg et al., 1991 J. Cell. Biol. 114:343–349) and neutrophil adhesion to cytokine-activated endothelial cells (Hallman et al., 1991 Biochem. Biophys. Res. Comm. 174:236–243; Smith, et al. 1991 J. Clin. Invest. 87:609–618; Spertini et al., 1991 J. Immunol. 147:2565–2573). Recently, neutrophil L-selectin has been shown to be a potential counter-receptor for E-selectin (Kishimoto et al., 1990 Blood 78:805–811; Picker et al., 1991 Cell 66:921–933).

L-selectin is constitutively expressed on resting neutrophils in a seemingly functional form. Freshly isolated neutrophils can bind to stimulated endothelium at a reduced temperature (4°–7° C.) in vitro (Hallmann et al., 1991. Biochem. Biophys. Res. Commun., 174, 236; Spertini et al., 1991 J. Immunol., 147:2565). However, within minutes of neutrophil exposure to low levels of chemotactic factors, L-selectin is rapidly down-regulated from the cell surface (Kishimoto et al., 1989 Science, 245:1238). Near complete down-regulation of L-selectin can be detected within minutes in vitro. This form of inverse regulation is achieved by proteolytic degradation of the L-selectin on the cell surface. A large fragment of L-selectin can be recovered from the supernatant of activated cells, suggesting that L-selectin is proteolytically clipped close to the transmembrane domain (Kishimoto et al., 1989 Science 245:1238).

Analysis of neutrophils which are recovered from the inflamed mouse peritoneum in vivo (Jutila et al., 1989 J. Immunol 143:3318) and immunohistological analysis of neutrophils in inflamed skin sites (Kishimoto et al., 1989 Science 245–1238), suggests that this inverse regulation of adhesion molecules occurs in vivo as well. Lymphocytes and monocytes can also shed L-selectin in vivo upon activation, although the kinetics are significantly slower (Jung et al., 1988 J. Immunol 141:4110; Jutila et al., 1990 Blood 76:178; Kishimoto et al., 1990 Proc. Nat'l Acad. Sci. USA 87:2244).

E-selectin is normally absent from endothelial cells. However, upon stimulation with inflammatory cytokines, endothelial cells express E-selectin within several hours. E-selectin is synthesized de novo, and is blocked by protein synthesis inhibitors (Bevilacqua et al., 1987 *Proc. Nat'l Acad. Sci.* USA 84:9238). This up-regulation of E-selectin is similar to that seen with other endothelial adhesion molecules, such as ICAM-1 and VCAM-1. However, in contrast to these other adhesion molecules which remain highly expressed for over 24 hours, E-selectin expression peaks at 3–4 hr and then is down-modulated by 8–24 hr in vitro (Bevilacqua et al., 1987 *Proc. Nat'l Acad. Sci.* USA 34:9238; Pobert et al., 1986 *J. Immunol* 137:1893). The time course of E-selectin expression is similar to the time course of neutrophil infiltration into acute inflammatory sites in vivo. These results suggest that E-selectin is involved primarily in the acute inflammatory response. E-selectin expression is also rapidly inducible in vivo and coincides with the influx of neutrophils (Norris et al., 1991 *J. Invest. Dermatol.* 96:763; Cotran et al., 1986 *J. Exp. Med.* 164:661; Munro et al., 1991 *Lab Invest.* 64:295; Redl et al., 1991 *Am. J. Pathol.* 139:461; Munro et al., 1989 *Am. J. Pathol.* 135:121; Leung et al., 1991 *J. Clin. Invest.* 87:1805). However, in some chronic inflammatory lesions, notably some inflamed skin and synovial sites, E-selectin expression is quite prominent (Cotran et al., 1986 *J. Exp. Med.* 164:661; Koch et al., 1991 *Lab. Inves.* 64:313; Picker et al., 1991 *Nature* 349:746; Norris et al., 1991 *J. Invest. Dermatol* 96:763). Unlike L-selectin, there is no in vitro evidence to suggest that E-selectin is shed from the endothelial surface.

At the molecular level, all three selectins exhibit a unique mosaic structure consisting of an N-terminal type-C lectin domain, an epidermal growth factor (EGF)-like domain, and multiple short consensus repeat (SCR) domains homologous to those found in complement regulatory proteins (Johnston et al., 1989 *Cell* 56:1033-1044; Bevilacqua et al., 1987 *Proc. Natl. Acad. Sci.* USA 84:9238–9242; Laskey et al., 1989 *Cell* 56:1045-1055; Siegelman et al., 1989 *Science* (Wash. D.C.) 243:1165-1172; Camerini et al., 1989 *Nature* (London) 342:78–80; Tedder et al., 1989 *J. Exp. Med.* 170:123-133). Overall these proteins share 40–60% identity at the nucleotide and amino acid level, and may have arisen by gene duplication of an early ancestral gene. The lectin domains of each selectin are believed to be critical to the adhesive functions of the proteins, and the carbohydrate binding specificities of all three selectins have been partially defined. P- and E-selectin both recognize sialylated Lewis x (sLex) which decorates glycoproteins and glycolipids expressed by myeloid cells although differences in their binding properties exist (Phillips et al., 1990 *Science* (Wash. D.C.) 250:1130–1132; Lowe et al., 1990 *Cell* 63:475–484; Goelz et al., 1990 *Cell* 63:1349–1356, Walz et al., 1990 *Science* 250:1132; Polley et al., 1991 *Natl. Acad. Sci.* 8:6224–6228). L-selectin function is blocked by certain simple sugars, such as mannose-6-$PO_4$, and certain complex polysaccharides, such as the mannose-6-$PO_4$, rich phosphomannan (phosphomannan monoester core i.e., PPME) from the yeast (*Hansenula holstii*, Yednock et al., 1987 *J. Cell. Biol.* 104:725–731; Imami et al., 1990 *J. Cell. Biol.* 111:1225–1232, rev. in Rosen, 1990, *Am. J. Respir. Cell. Mol. Biol.*). Furthermore, many antibodies which block L-selectin function recognize epitopes encoded by the lectin domain (Bowen et al., 1990 *J. Cell. Biol.* 110:147–153; Kansas, et al. 1991 *J. Cell. Biol.* 114:351–358).

Other spatially separate and distinct functional domains of the selectins may also exist. Antibodies against the mouse or human L-selectin EGF domain block lymphocyte adhesion to HEV, but have little effect on carbohydrate binding (Kansas et al., 1991 *J. Cell Biol.* 114:351–358; Siegelman et al., 1989 *Cell* 61:611–622). Studies of chimeric L-selectin/ immunoglobulin constructs suggest that the SCR domains also have important functional roles for selectins (Watson et al., 1991 *J. Cell. Biol.* 115:235–243), but in contrast to the lectin and EGF domains, no function blocking antibodies have been shown to recognize this region. In addition, it is thought that the functional role of the SCRs is restricted to maintenance of proper molecular conformation, which is distinct for each selectin (Watson et al., 1991 *J. Cell. Biol.* 115:235–243).

Even though many anti-selectin mAbs have been developed, none have been shown to have the ability of recognizing determinants on two distinct selectins. CL2, which recognizes human E-selectin, reacts with dog L-selectin, but not both in the same animal (Abbassi et al., 1991 *J. Immuno.* 147:2107–2115). Spertini et al. (1991 *J. Immunol.* 147:942) provide the functional characterization and molecular localization of at least 11 different epitopes on L-selectin, but again none of these are expressed on two different selectins. TQ-1 and Leu-8, which recognize L-selectin, also show a much more restricted pattern of staining and do not stain other selectins. None of the published anti-E-selectin or P-selectin mabs have been shown to react with other selectins. It is intriguing that even though there is a significant level of identity at the amino acid level between the different selectins and a large number of anti-selectin mAbs have been generated, prior to this invention, no antibody has been reported to recognize an epitope shared by two different selectins.

As the primary mediators of the acute inflammatory response, neutrophils represent an essential component of the immune system. Neutrophils arise in the bone marrow, which contains a large pool of readily mobilized mature granulocytes. After release into the blood, neutrophils have a relatively short half-life (4 to 10 hr. in humans) where they exist in dynamic equilibrium between a freely blood-borne pool and a marginating pool of cells interacting reversibly with the endothelium. In response to acute inflammatory stimuli, neutrophils adhere tightly to the vascular endothelium, migrate through the vessel wall, and subsequently move along a chemotactic gradient toward the inflammatory stimulus where they respond phagocytically. The interaction of neutrophils and vascular endothelial cells is thus an essential initial step in the acute inflammatory response.

While the inflammatory response of leukocytes is vital to the eradication of invading microorganisms, a substantial and convincing body of evidence indicates that inflammatory phagocytes also cause damage to various organs and tissues when these cells are activated in vivo by soluble inflammatory factors that are generated by inciting pathological events (Harlan, 1985 *Blood* 65:513–525). The adhesion and spreading of activated neutrophils and mononuclear phagocytes to vascular endothelial cells with the subsequent release of toxic oxidative metabolites and proteases has been implicated in the organ damage observed in diseases, such as, adult respiration distress syndrome (ARDS; shock lung syndrome), glomerulonephritis, acute and chronic allograft rejection; inflammatory skin diseases; rheumatoid arthritis; asthma, atherosclerosis, systemic lupus erythematosus, connective tissue diseases; vasculitis; and ischemia-reperfusion syndromes (ie. limb replantation, myocardial infarction, crush injury, shock, stroke, and organ transplantation). (Reviewed in Harlan, ibid.)

"Anti-Adhesion" therapy represents a novel approach for the treatment of those inflammatory and immune disorders where leukocyte adhesion to epithelium significantly contributes to vascular and tissue injury/damage. The present invention specifically interacts with and blocks the adhesion process, and is therefore potentially useful for such disorders.

"Anti-Adhesion" therapy has a profound effect on the inflammatory response. Skin lesions can be reduced (Arfors et al., 1987 *Blood* 69:338), brain edema and death produced by bacterial meningitis can be reduced (Tuomanen et al., 1989 *J. Exp. Med.* 170:959), tissue edema associated with delayed-type hypersensitivity reactions can be reduced (Lindbom et al., 1990 *Clin. Immunol. Immunopath.* 57:105), airway hyperresponsiveness in allergic asthma can be reduced (Wegner et al., 1990 *Science* 247:456), remote lung injury following aspiration can be reduced (Goldman et al., 1991 *FASEB J.* 5:A509), late-phase bronchoconstriction following antigen challenge can be reduced (Gundel et al., 1991 *J. Clin. Invest.* 88:1407), permeability edema in acute lung inflammation can be reduced (Mulligan et al., 1991 *J. Clin. Invest.* 88:1396) and the development of auto-immune diabetes can be inhibited (Hutchings et al., 1990 *Nature* 346,639). "Anti-Adhesion" therapy can also prolong cardiac allograft survival (Flavin et al., 1991 *Transplant, Proc.* 23:533), attenuate lung damage and dysfunction secondary to oxygen toxicity (Wegner et al., 1991 *Am. Rev. Respir. Dis.* 143:A544), attenuate renal allograft rejection (Cosimi et al., 1990 *J. Immunol.* 144:4604), ameliorate antigen-induced arthritis (Jasin et al., 1990 *Arthritis Rheum.* 33:S34), protect against vascular injury and death in endotoxic shock (Thomas et al., 1991 *FASEB J.* 5:A509), and prevent second degree burns from becoming third degree burns (Bucky et al., 1991 *Proc. Amer. Burn Assoc.* 23:133).

Such "anti-adhesion" therapy is also efficacious in ischemia and reperfusion injury. Such therapy can be used to reduce permeability edema following ischemia-reperfusion (IR) of intestine (Hernandez et al., 1987 *Am J. Physiol.* 253:H699), to reduce myocardial damage following myocardial infraction (Winquist et al., 1990 *Circulation* 82:III; Ma et al. 1990 *Cir. Res.* 82:III), to reduce vascular and tissue damage following hemorrhagic shock and resuscitation (Mileski et al., 1990 *Surgery* 108:206), to reduce central nervous system damage following I/R of the spinal cord (Clark et al., 1991 *Stroke* 22:877), to reduce edema and tissue damage following frostbite and rewarming (Mileski et al., 1990 *Proc. Am. Burn Assoc.* 22:164), and to reduce infarct size following I/R of myocardium (Simpson et al., 1990 *Circulation* 81:226).

Monoclonal antibodies to L-selectin prevent neutrophil emigration into inflamed skin (Lewinsohn et al., 1987 *J. Immunol.* 138:4313), prevent neutrophil and monocyte emigration into inflamed ascites (Jutila et al., 1989 *J. Immunol.* 143:3318), and inhibit neutrophil emigration into inflamed peritoneum. Monoclonal antibodies to E-selectin inhibit neutrophil migration to the lung and thus provide a basis for their use in prevention or treatment of asthma (Gundel et al., 1991 *J. Clin. Invest;* Mulligan et al., 1991 *J. Clin. Invest.* 88:1396). Jasin et al. provide support for the use of antibodies in inhibiting neutrophil accumulation in inflamed synovium (Jasin et al., 1990 *Arthritis Rheum.* 33:S34; Koch et al., 1991 *Lab. Invest.* 64:313), among other specific cell effects.

There exists a longstanding need for the production of monoclonal antibodies, or active fragments thereof, reactive with an epitope or antigenic determinant shared by different selectin molecules, thus permitting the effective diagnosis, prophylaxis, and treatment of the multitude of diseases related to the inflammatory and the immune response. It is beneficial to have available mAbs which can recognize multiple members of this family of cell adhesion molecules, thus providing a broader range of applicability to such diseases and injuries.

SUMMARY OF THE INVENTION

The present invention relates to antibodies, antigen-binding fragments of the antibodies, and their biological equivalents that react with a domain that is present on different adhesion molecules and the cells that produce the antibodies.

The present invention also relates to antibodies, antigen-binding fragments of the antibodies, and their biological equivalents that react with a domain that is present on different selectins and the cells that produce the antibodies.

The antibodies of the present invention react with the different selectins including cells bearing or expressing the different selecting.

The antibodies, antigen-binding fragments of the antibodies and their biological equivalents bind to cells bearing or expressing the different selectins and inhibit the function of the different selecting.

The present invention also relates to the use of the antibodies as therapeutic agents in preventing or treating diseases wherein selectins play a role. Such diseases include but are not limited to inflammatory diseases, allergies, autoimmune diseases, asthma, arthritis and ischemia-reperfusion injury. Of particular interest is the prevention or inhibition of ischemia-reperfusion injury in the lung using the antibodies or their functional equivalents in an effective amount. Such treatment is also effective in reducing mortality in those mammals so afflicted.

The present invention also encompasses methods of detecting cells bearing or expressing different selectins. Such methods are useful for diagnosis of diseases where selectins and selectin-bearing cells play a role, and for monitoring the progression of such diseases.

Such methods are also useful for monitoring the efficacy of therapeutic agents during the course of treatment of a disease where selectins and selectin-bearing cells play a role.

The present invention encompasses antibodies, antigen binding fragments and chimeric antibodies that recognize a common antigen determinant on E-selectin and L-selectin. Antibodies of the present invention and their functional equivalents are capable of inhibiting both E-selectin and L-selectin mediated cell-cell interactions.

The present invention encompasses methods that simultaneously or individually inhibit or modulate the functions of E-selectin and L-selectin, using antibodies or their functional equivalents that are capable of binding to E-selectin and L-selectin.

The present invention are antibodies and their functional equivalents that are capable of inhibiting neutrophil binding to cells expressing E-selectin as well as capable of preventing or inhibiting neutrophil rolling on endothelial cell layers expressing E-selectin.

The present invention are antibodies and their functional equivalents that are capable of preventing, inhibiting or modulating lymphocyte homing to peripheral lymphoid tissues.

BRIEF DESCRIPTION OF THE DRAWINGS

These and other objects, features, and many of the attendant advantages of the invention will be better understood upon a reading of the following detailed description when considered in connection with the accompanying drawings wherein:

FIG. 10A slows that neutrophils treated with EL-246 stained brightly with the FITC-second stage before the assay. FIG. 10B shows the lack of staining of the FITC-second stage antibody of the same cells after the assay. FIG. 10C shows the cells analyzed in 10B, stained with a second anti-L-selectin mAb (DREG56). FIG. 10D shows the lack of staining of the E-selectin transfectants with the FITC-second stage before the assay and FIG. 10E shows staining after the assay. FIG. 10F represents the results of a conventional indirect stain of the transfectant for E-selectin. The dotted lines in each histogram represent background fluorescence after staining with negative control antibodies.

FIG. 12A represents the binding of the transfectants to PLN HEV, and FIG. 12B shows the effects of EL-246 on binding to the same vessels in serial sections. Arrows point to the same vessel in the serial section Magnification 200×.

DETAILED DESCRIPTION OF THE INVENTION

Figure 1:
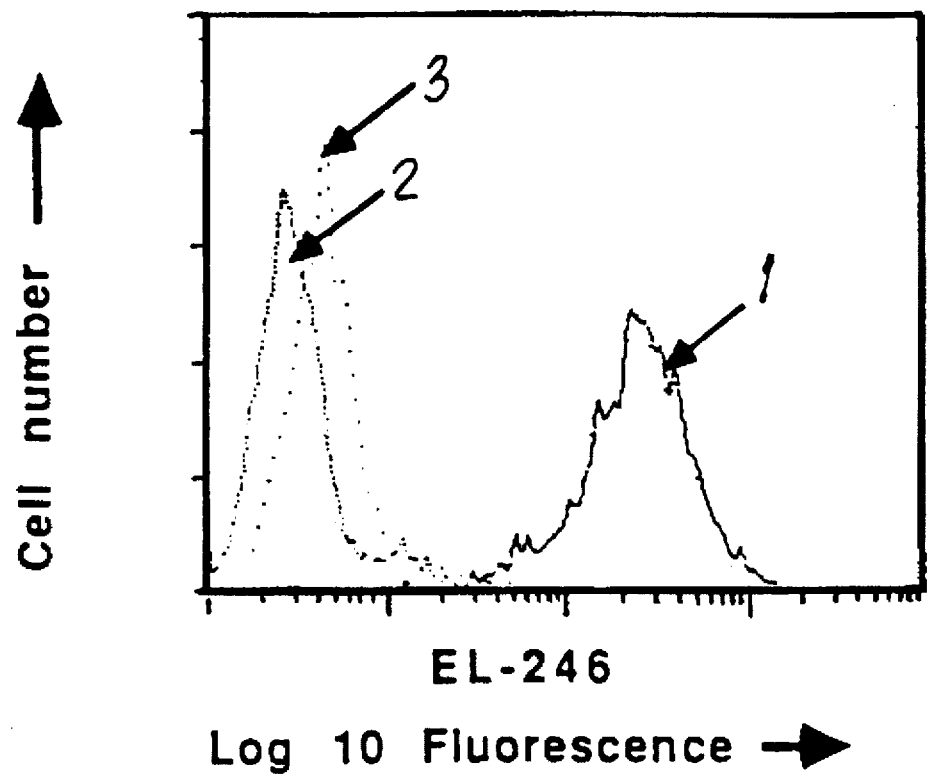
FIG. 1. Shows that EL-246 staining L1-2 cells transfected with human E-selectin cDNA. The arrows point to histograms which represent (1) EL-246 staining of L1-2ELAM and (2) L1-2 transfectant controls, and (3) background staining (second stage control) of the L1-2ELAM transfectants.

The present invention includes monoclonal antibodies (mAbs), antigen-binding fragments and their functional equivalents which bind to a common antigenic determinant or epitope found on separate and distinct adhesion molecules. The present invention also includes cells capable of producing mAbs which are capable of recognizing common antigenic determinants present on separate and distinct adhesion molecules. This invention includes mAbs capable of binding to common determinants found on selectins, preferably common determinants on E selectin and L-selectin and cells capable of expressing such antibodies. This invention also involves a novel monoclonal antibody, EL-246, and the cells capable of producing the novel mAb. The cells producing monoclonal antibody EL-246 were deposited on May 22, 1992 under the terms of the Budapest Treaty with the American Type Culture Collection (ATCC), 12301 Parklawn Drive, Rockville, MD, 20852, USA, under Accession No: HB 11049.

The present invention involves monoclonal antibodies and their functional equivalents which bind one or more epitopes present on the short consensus repeat (SCR) domain of both L-selectin and E-selectin and the cells capable of producing the mAbs.

The invention includes the antibodies and all biologically-active fragments thereof, including Fab and F(ab')$_2$ fragments. Of special interest to the present invention are antibodies capable of binding to separate and distinct adhesion molecules, preferably antibodies capable of binding to separate and distinct selecting, most preferably antibodies capable of binding to both E- and L-selectin which are produced in humans, or are "humanized" (i.e., nonimmunogenic in a human) by recombinant or other technology. Humanized antibodies may be produced, for example, by replacing an immunogenic portion of an antibody with a corresponding, but nonimmunogenic portion (i.e., chimeric antibodies). Such chimeric antibodies may contain the reactive or antigen binding portion of an antibody from one species and the Fc portion of an antibody (nonimmunogenic) from a different species. Examples of chimeric antibodies, include but are not limited to, non-human mammal-human chimeras, rodent-human chimeras, murine-human and rat-human chimeras (Robinson et al., International Patent Application 184,187; Taniguchi M., European Patent Application 1717,496; Morrison et al., European Patent Application 173,494; Neuberger et al., PCT Application WO 86/01533; Cabilly et al., European Patent Application 125,023; Better et al., 1988 *Science* 240:1041; Liu et al., 1987 *Proc. Natl. Acad. Sci.* USA 84:3439; Nishimura et al., 1987 *Canc. Res.*

47:999; Wood et al., 1985 *Nature* 314:446; Shaw et al., 1988 *J. Natl. Cancer Inst.* 80: 1553, all incorporated herein by reference).

General reviews of "humanized" chimeric antibodies are provided by Morrison S., 1985 *Science* 229:1202 and by Oi et al., 1986 *BioTechniques* 4:214.

Suitable "humanized" antibodies can be alternatively produced by CDR or CEA substitution (Jones et al., 1986 *Nature* 321:552; Verhoeyan et al., 1998 *Science* 239:1534; Beidler et al., 1998 *J. Immunol.* 141:4053, all incorporated herein by reference).

The invention further provides methods for employing such compounds in the diagnosis, prevention and treatment of diseases, such as but not limited to those associated with the inflammatory and immune response, ARDS, glomerulonephritis, acute and chronic allograft rejection, inflammatory skin diseases, rheumatoid arthritis, asthma, atherosclerosis, systemic lupus erythematosus, connective tissue diseases, vasculitis, ischemia-reperfusion injury and cancer. The invention further provides a new research tool for the study of leukocyte-endothelium interactions and the role of adhesion molecules in disease mechanisms.

Mammalian lymphocytes are immunized by in vivo immunization of the animal or in vitro contact with whole cells, cell extracts expressing adhesion molecules or with isolated adhesion molecules or fragments thereof. Monoclonal antibodies of the present invention which recognize both E-selectin and L-selectin are generated in response to the appropriate antigenic stimulus or immunogen. For production of the antibodies of the present invention the immunogen in the form of naturally occurring cells that express selectins, cells transfected or transformed with L- and/or E-selectin or the selectin proteins and peptides, alone or conjugated other proteins, liposomes or the like. The immunogen contains protein regions common to both E-selectin and L-selectin, more preferably the immunogen contains the SCR domain or fragments thereof.

In one embodiment, a single cell type stably expressing both human E-selectin cDNA and L-selectin cDNA is used as the immunogen for generating antibodies that react with both E- and L-selectin.

In another embodiment, cells stably expressing human L-selectin cDNA are used as the immunogen. In a further embodiment of the present invention, cells stably expressing the human SCR domain or a portion thereof are used as the immunogen. In another embodiment, mouse lymphoma cells stably expressing human E-selectin cDNA are used as the immunogen for the generation of antibodies that react with both E-selectin and L-selectin. In another embodiment, endothelial cells expressing E-selectin following cytokine-stimulation or peripheral blood leukocytes expressing L-selectin are used as the immunogen.

For in vivo immunizations, immunizations are repeated as necessary at intervals of up to a few weeks (e.g., 2–4 weeks) so as to obtain a sufficient titer of antibodies. The cells, cell extracts or antigenic adhesion protein, peptides or fragments are carried in appropriate solutions or adjuvants. Following the last antigen boost, the animals are sacrificed and the spleen cells are removed.

Hybridoma formation and monoclonal antibody production may be effected by many different techniques which are well-known in the art. Basically, the process involves first obtaining immune cells, such as those from the spleen of a mammal, which have been previously stimulated with an antigen or immunogen either in vivo or in vitro. These cells are then fused to cells, such as myeloma cells or transformed cells, which are capable of replicating indefinitely in cell culture, thereby producing an immortal, immunoglobulin-secreting cell line. The immortal cells or myeloma cells, which is preferably murine, but may also be derived from cells of other mammalian species, including but not limited to rats and humans, is selected to be deficient in enzymes necessary for the utilization of certain nutrients, to be capable of rapid growth and to have good fusion capability. Many such cell lines or myelomas are known to those skilled in the art, and others are regularly described. Enzyme deficiencies may include, for example, thymidine kinase (TK) or hypoxanthine-guanine phosphoriboxyl transferase (HGPRT). These deficiencies allow selection for fused cells according to their ability to grow on, for example, hypoxanthine aminopterinthymidine medium (HAT). Preferably, the immortal fusion partners utilized are derived from a line which does not secrete immunoglobulin. The resulting fused cells, or hybridomas, are cultured under conditions which allow for the survival of fused but not unfused cells and the resulting colonies screened for the production of the desired monoclonal antibodies. Colonies producing such antibodies are cloned, expanded, and grown either in vivo or in vitro so as to produce large quantities of antibody (for description of the theoretical basis and practical methodology of fusing such cells, see Köhler and Milstein, 1975 *Nature* 256:495, the disclosures of which are hereby incorporated by reference). While such methods are described in further detail hereinafter, it will be appreciated by those skilled in the art that modifications and additions of the techniques may be made without departing from the scope of the present invention.

Individual fused cells may be grown in individual tissue culture wells. Feeder cells, such as irradiated thymocytes or other cells, may be used to increased the viability of the cells. Hybridoma culture supernatants form the individual wells are assayed for antibody binding to human cell adhesion molecule cDNA transfected mammalian cells or leukocytes or the purified adhesion molecules or fragments thereof using suitable detection methods known in the art, such as enzyme-linked immunoassay (EIA) and immunodot assay. For the former, culture supernatants are placed in reaction cells which have been coated with the specific cell adhesion molecules (CAM) to which an antibody is to bind. After incubation, the reaction wells are washed, and remaining antibody bound to the antigen is detected through a labelled antibody reactive with the anti-CAM antibody. Appropriate labels include radioisotopes, luminescent substrates such as fluorescing agents and components of enzymatic labels.

The Immunodot method may also be utilized to screen for clones expressing anti-CAM antibodies (Towbin et al., 1984 *Immunol. Method* 72:313, the disclosures of which are hereby incorporated by reference). Purified CAM is applied to cellulose nitrate membrane as "dots" and allowed to dry. After blocking of non specific binding sites with a gelatin solution, the membranes are sequentially immersed in culture supernatant, an antimouse immunoglobulin-peroxidase conjugate solution and a 4-chloro-1-naphthol solution, with phosphate-buffered saline (PBS) washes in between. Clones expressing reactive immunoglobulin appear as colored dots. Other screening systems known to those in the art may be utilized.

Large quantities of monoclonal antibodies from secreting hybridomas may be produced by injecting the clones into the peritoneal cavity of mice and harvesting the ascites fluid therefrom. The mice, preferably primed with pristine or some other tumor-promoter and immunosuppressed chemically or by irradiation, may be of various strains, preferably New Zealand Black or Balb/c strains. The ascites fluid is harvested from the mice and the monoclonal antibody purified therefrom, for example, by CM Sepharose column or other chromatographic means. High titers of antibodies may be so recovered. Alternatively, the hybridomas may be cultured in vitro or as suspension cultures, both in batch or continuous culture processes, and monoclonal antibodies recovered from the culture medium or supernatant.

The antibodies or antigen binding fragments may also be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of bacteriophages, each containing one heavy chain gene and one light chain gene retaining the initial antigen specificity, is produced using the cDNA. A combinatorial library is constructed by combining the heavy chain gene library with the light chain gene library. This results in a library of clones which coexpress a heavy and light chain (resembling the Fab fragment or antigen binding fragment of an antibody molecule).

The phages that carry these genes are transfected into bacteria. When antibody gene synthesis is induced in the transfected bacteria, the heavy and light chain proteins self-assemble to produce active antibodies that can be detected by screening with the antigen or immunogen.

The technology for expression both heavy and light chain in *E. coli* is the subject of the PCT patent applications; publication numbers WO 901443, WO 901443, and WO 9014424 and in Huse et al., 1989 *Science* 246:1275–1281, incorporated herein by reference.

In addition to recognizing or binding both E-selectin and L-selectin, the monoclonal antibodies of the present invention block the adhesive functions of both molecules. In one embodiment, the present invention is a novel mAb (EL-246) that recognizes a common epitope expressed on both human E- and L-selectin. EL-246 blocks the function of both proteins, recognizes selectins from a variety of different animals, and its epitope is present within or requires the SCR domains of both E- and L-selectin. The present novel antibodies that react with the SCR domains inhibit the adhesive function of two distinct selectins.

Lymphocyte adhesion (L-selectin-dependent) to peripheral lymph node HEV (E-selectin-dependent) was blocked by >95% with EL-246. This inhibition was greater than that by DREG 56 anti-L-selectin blocking mAb (88%) which is an antibody that only reacts with L-selectin and not E-selectin (Kishimoto et al., 1990 *Proc. Natl. Acad. Sci. USA* 87:2244–2248). The carbohydrate (PPME) binding activity of L-selectin was not appreciably inhibited by EL-246 indicating the specificity of EL-246 for the SCR domain. EL-246 effectively blocks (>90%) the capacity of E-selectin, expressed in adherent L-cells, to bind human neutrophils.

The present invention may be especially useful as a therapeutic agent in acute settings, such as myocardial infarction, antigen-stimulated asthmatic reactions, or shock, or even in subacute settings such as allograft rejection. This mAb may also be an effective treatment for chronic disorders such as rheumatoid arthritis.

The antibodies or antigen binding fragments of the present invention are a useful method of prevention or treatment of asthma in mammals. The method of preventing or treating asthma using anti-selectin antibodies is detailed in U.S. Ser. No. 738,633 filed on Jul. 31, 1991, and in Gundel et al., 1991 *J. Clin. Invest.* 88:1407–1411 which are incorporated herein by reference. The antibodies or antigen binding fragments inhibit the late-phase airway obstruction which often accompanies antigen-induced asthmatic reactions. The adhesion molecule, E-selectin, mediates this phase of the reaction. Blockage of this phase by the present invention serve as a treatment to prevent obstruction of the lung airways. The antibodies or antigen binding fragments are administered in a therapeutic dosage of 1 pg/kg to 10 mg/kg body weight by bolus intravenous injection prior to or during exposure to an antigen.

Many pathogens or disease causing microorganisms use cell surface adhesion molecules as a means of attachment to mammalian cells. Antibodies or antigen binding fragments and their biological equivalents of the present invention may be effective in blocking or inhibiting adhesion molecule-mediated binding of pathogens to mammalian cells. Moreover, antibodies, antigen binding fragments, and their biological equivalents of the present invention may be effective in blocking or inhibiting E- and L-selectin-mediated binding of pathogens to mammalian cells. Such disease causing microorganisms, include but are not limited to, viral, parasitic, bacterial, and fungal pathogens, and the like.

Monoclonal antibodies of the present invention are useful as a research or investigational tool in determining the diverse functional activity of selectins.

Insight into the diverse functional activity of E- and L-selectin, and the potential "homotypic" interaction of these proteins, may be gained by further analysis of the EL-246 epitope. Neutrophil adhesion to cytokine-activated endothelial cells can be blocked by anti-E-selectin as well as anti-L-selectin mAbs (Bevilacqua et al., 1987 *Proc. Natl. Acad. Sci. USA* 84:9239–9241; Bevilacqua et al., 1989 *Science* (Wash. D.C.) 243:1160–1112; Hallman et al., 1991 *Biochem. Biophys, Res. Comm.* 174:236–243; Smith et al., 1991 *J. Clin. Invest.* 87:609–618; Spertini et al., 1991 *J. Immunol.* 147:2565–2573). Kishimoto et al., 1990 *Blood* 78:805–811 showed that certain anti-E- and L-selectin mAbs are not additive in their blocking effects on neutrophil-activated endothelial cell adhesion, suggesting that these two proteins participate in the same adhesion pathway, perhaps as receptor-counterreceptor pairs. This hypothesis is supported by the observation that neutrophil binding to E-selectin cDNA transfected L-cells is blocked by anti-L-selectin mAb treatment of the leukocyte (Kishimoto et al., 1990 *Blood* 788:805–811). Picker et al. (1991 *Cell* 66:921–933) extended these findings by demonstrating that L-selectin on neutrophils is decorated by sLex carbohydrates and may preferentially present these structures to E-selectin. In contrast, Spertini et al., (1991 *J. Immunol.* 147:2565–2573) have also demonstrated that neutrophil-activated endothelial cell adhesion involves E- and L-selectin, but they found that mAbs to these proteins have additive blocking effects, suggesting separate adhesion pathways. Since EL-246 is an effective blocker of E- and L-selectin function and recognizes a different molecular region (see below) than the blocking mAbs used in the above studies, it may be useful in determining the basis for some of the discrepancies in the different reports.

Domain mapping studies using L-selectin/P-selectin chimeric proteins localized the EL-246 epitope to the SCR domain of L-selectin. The epitope on E-selectin recognized by the EL-246 mAb may also reside within the SCR domains of this selectin. The location of the EL-246 epitope in the SCRs is consistent with the inability of EL-246 to block carbohydrate PPME binding and with recent reports indicating that the SCR domains of L- and E-selectin are essential for optimal adhesive function (Watson et al., 1991 *J. Cell. Biol.* 115:235-243; Pigott et al., 1991 *J. Immunol.* 147:130). As mentioned in the background section, the lectin domain of the selectins is required for function and many blocking anti-selectin mAbs recognize epitopes encoded by this region (Bowen et al., 1990 *J. Cell. Biol.* 110:147-153; Kansas et al., 1991 *Cell. Biol.* 114:351-358; Kishimoto et al., 1990 *Proc. Natl. Acad. Sci.* USA 87:2244-2248). MAb for epitopes localized in the EGF domain have been shown to inhibit adhesion mediated by L-selectin. (Polley et al., 1991 *Natl. Acad. Sci.* USA 88:6224-6228; Bowen et al., 1990 *J. Cell. Biol.* 110:147-153; Kansas et al., 1991 *Cell. Biol.* 114:351-358; Siegelman et al. 1990 *Cell.* 61:611). The data presented here extends those observations, and demonstrates that mAbs to appropriate epitopes within each extracellular domain of selectins can inhibit adhesive function.

Without being bound by theory, it is possible that mAbs inhibit adhesion as a result of direct interference with ligand binding or that binding of mAb, especially those mAbs which define epitopes outside the lectin domain, might perturb the conformation of the protein so as to indirectly impair the functional integrity of the lectin domain. If EL-246 blocks adhesion by altering the functional conformation of the selectins, this would suggest that the role of the SCRs in adhesion is similar for E- and L-selectin. This is in contrast to Watson et al. (1991 *J. Cell. Biol.* 115:234-243) who predicted that the role of the SCRs is unique for each selectin. Since EL-246 only recognizes E- and L-selectin, this latter prediction may be true for P-selectin. Thus, in addition to having greater numbers of SCR domains (9 versus 6 and 2 in E- and L-selectin, respectively) there may exist molecular differences in P-selectin SCRs which contribute to the unique functions of this molecule, such as adhesion of thrombin-activated platelets.

Additional molecular and functional characterization of the epitope recognized by EL-246 will lead to new insights into the function of the selectins and the evolutionary conservation of this family of adhesion proteins. Targets for treatments may be designed to regulate or block the epitope that is recognized by EL-246 thus regulating selectin activity in vivo. Importantly, new therapeutics which inhibit this site have the added advantage of blocking the activity of leukocyte-endothelial cell adhesion by simultaneously inhibiting both leukocyte as well as endothelial cell adhesion proteins.

The monoclonal antibodies so produced have a number of diagnostic and therapeutic uses. They can be used in in vitro diagnostic agents to test for the presence of adhesion molecules, preferably selecting, present in insoluble form or associated with cells in mammals by subjecting biological samples or tissues or other human-derived substances to standard immunoassay protocols. The antibodies or antigen binding fragments are also useful in analysis of tissue biopsy material such as high endothelial venules, lung tissue, or any site of inflammation to detect the presence of the cells bearing the reactive epitopes. Such assays may be of a radioimmunoassay, EIA, fluorescent or chemiluminescent format or the like. In one such assay, biological sample is contacted to antibodies of the present invention and a labelled second antibody used to detect the presence of the selectin to which the antibodies are bound. In addition, many histochemical methods can be employed and are well-known in the art.

One particular assay utilizes the monoclonal antibody, EL-246 in standard techniques known in the art to carry out an enzyme-linked immunoassay as described in *Methods in Immunodiagnosis*, 2nd edition, Rose and Bigazzi, Eds., John Wiley and Sons, 1980, which is incorporated by reference, and in Campbell et al., *Methods of Immunology*, W. A. Benjamin, Inc., 1964. Such assay may be, for example, of direct format (where the labeled first antibody is reactive with the antigen), an indirect format (where a labeled second antibody is reactive with the first antibody), a competitive format (such as the addition of a labeled antigen), or a sandwich format (where both labeled and unlabeled antibody or utilized), as well as other formats described in the art.

In one embodiment, biological sample from a mammal is applied to an insoluble matrix or solid substrate, so as to bind the selectin on selectin-bearing cells to this matrix. This matrix is washed using a physiological buffer, such as phosphate buffered saline (PBS), to remove unbound materials. The solid antigen-bound matrix is exposed to a solution having therein an antibody of the present invention such as monoclonal antibody EL-246. The antibody is allowed to react with the antigens on the solid matrix, and the matrix is again washed to remove any unbound antibody. This complex is then exposed to a solution having therein a labeled second antibody such as goat anti-mouse IgG which is reactive with the first antibody. This antibody is preferably labeled with a component of an enzymatic reaction, such as peroxidase; a radioisotope, such as $^{125}$I; or a chemiluminescent or fluorescent substrate. The complex is again washed to remove any unbound antibody. The reaction is monitored by a means appropriate for the label chosen, such as a scintillation counter or a spectrophotometer. Biological samples appropriate for such a detection assay include, but are not limited to, tissue biopsy extracts, whole blood, plasma, serum, cerebral spinal fluid, synovial fluid, plural fluid, urine and the like.

In another embodiment, the antibodies of the present invention are applied to an insoluble matrix or solid substrate, so as to bind the antibodies to the matrix. A biological sample suspected of containing L- and/or E-selectin-bearing or lysates of such cells is added to the matrix and allowed to react with the antibodies on the matrix to form a selectin-antibody complex. The complex is detected using a labeled second antibody. The labeled second antibody is EL-246 or a biologically equivalent antibody. This method detects both L- and E-selectin, and L- and E-selectin-bearing cells if they are present in the biological sample. The assay is both qualitative or quantitative. The assay may be modified to differentiate between L-selectin and E-selectin by using monoclonal antibodies specific for the individual selectin of interest. Such monoclonal antibodies are DREG mAbs as described in Kishimoto et al., 1990 *Proc. Natl. Sci.* 87:2244-2248.

The methods for detecting and quantifying L- and/or E-selectin bearing cells in biological samples are particularly useful in diagnosing disease states such as inflammatory diseases, autoimmune diseases, cancer, asthma, ischemia reperfusion injury and the like. The methods are also useful for monitoring the progression of these disease states. Moreover, the method is useful for monitoring the efficacy of therapeutic agents such as anti-inflammatory agents, chemotherapeutic agents, anti-adhesive agents and the like, during the course of treatment.

For all such therapeutic, prophylactic and diagnostic uses, the monoclonal antibodies and other necessary reagents and appropriate devices and accessories may be provided in kit form so as to be readily available and easily used.

The antibodies of the present invention can be formulated into pharmaceutical preparations having therapeutic, diagnostic or other uses in mammals. The antibodies or antigen binding fragments of the present invention are especially useful in the prevention and/or treatment of mammals with coronary heart disease or those in high risk categories for heart attack or stroke such as those with high blood pressure, diabetes, high cholesterol, or smokers.

The antibodies or antigen binding fragments of the present invention are also useful for the prevention or treatment of ischemia-reperfusion injury which occurs during or after surgery, especially after coronary bypass surgery.

The antibodies, antigen binding fragments and their functional equivalents are especially useful in prevention or inhibition of lung ischemia/reperfusion injury. The present invention has been shown to be an effective therapeutic agent in preventing or inhibiting loss of lung function and preventing mortality in mammals treated with an antibody that is capable of binding to E-selectin and L-selectin.

Mammals in need of treatment for lung ischemia/reperfusion injury as in the case of a lung transplant are administered an amount of antibody or their functional equivalent that is effective in preventing or inhibiting loss of lung function and preventing mortality. Such treatment of mammals prevents, inhibits, or attenuates an inflammatory response at the affected site.

The antibodies or antigen binding fragments of the present invention are also useful for the prevention or treatment of allergic rhinitis, asthma and anaphylaxis. The present antibodies are also useful in prevention or treatment of inflammatory diseases and autoimmune diseases such as Rheumatoid arthritis, Systemic lupus erythematosus, Juvenile diabetes, Sjögren syndrome, connective tissue diseases and the like.

The antibodies of the present invention, antigen binding fragments and their functional equivalents are effective in preventing or inhibiting cell-cell interactions mediated by E-selectin and/or L-selectin. The antibodies inhibit neutrophil L-selectin interactions with cells expressing E-selectin including activated endothelial cell layers, E-selectin cDNA transfectants and the like. The antibodies of the present invention prevent or inhibit E-selectin mediated neutrophil rolling on endothelial cell layers, such cell layers present in arteries, veins, capillaries, lymphoid vessels and the like. Such inhibitory effects produced by the antibodies and their functional equivalents are useful in preventing, inhibiting or modulating an inflammatory response.

The antibodies of the present invention and their functional equivalents are capable of preventing or inhibiting the binding of E-selectin expressing cells to high endothelial venule cells (HEV) present in peripheral lymph nodes.

Using a xenogeneic in vivo homing model, it was found that lymphocytes from humans, goats, sheep and cows home in a tissue-specific fashion to lymphoid tissues of mice after injection intravenously. These results are not surprising, since earlier observations showed that homing mechanisms are highly conserved between mammals (Spertini, O et al. 1991. *J. Immunol.* 147:942; Wu, N. W. et al. 1988. *J. Cell Biol.* 107:1845; Walcheck, B. et al. 1992 *Eur. J. Immunol.* 22:469).

One aspect of the present invention is a method to prevent or inhibit lymphocyte homing to lymphoid tissue in a mammal. The antibody of the present invention inhibits the ability of lymphocytes to home to lymphoid tissue.

Leukocytes may deliver EL-246 to sites that specifically express E-selectin. In assays where neutrophils were pre-coated with EL-246, washed, and added to either E-selectin cDNA transfectants or cytokine-activated HUVECs, the mAb transferred from the leukocyte to E-selectin. The amount of EL-246 on the E-selectin transfectants, as measured by staining with FITC-anti-mouse second stage followed by flow cytometry after transferring from the leukocyte was greater than the amount after directly staining the transfectants with saturating levels of EL-246. Shedding of surface L-selectin bound EL-246 did not account for these results, because the neutrophils which lost EL-246 still stained brightly with anti-L-selectin mAb DREG 56. It is unlikely that DREG 56 reacted with new L-selectin that was translocated to the cell surface during the course of the assay because 1) the assay time was relatively short (15 min) and 2) significant intracellular pools of preformed L-selectin have not detected in any previous analyses of neutrophils (Jutila, M. A. et al. 1989. *J. Immunol* 143:3318; Kishimoto, T K et al. 1990 *Proc. Natl. Acad. Sci.* USA 87:2244; Jutila, M. A. et al. 1990. *Cell Immunol.* 132:201; Kishimoto, T. K. et al 1989 *Science* 245:1238). Once neutrophils have lost L-selectin in vitro, they normally die before new expression is seen. If EL-246 transfers from L-selectin to E-selectin when these molecules come in close association, then leukocytes may be an efficient delivery system for the mAb in vivo.

The antibodies and antigen binding fragments of the present invention are useful in prevention and treatment of infections and diseases caused by pathogenic or potentially pathogenic microorganisms. Pharmaceutical compositions comprising the antibodies, antigen binding fragments of the antibodies or their biological equivalents are administered to host mammalian cells bearing adhesions molecules, preferably selecting, most preferably, L- or E-selectin.

In providing a patient with the antibodies or antigen binding fragments of the present invention to a recipient mammal, preferably a human, the dosage of administered antibodies or antigen binding fragments will very depending upon such factors as the mammal's age, weight, height, sex, general medical condition, previous medical history, etc. In general, it is desirable to provide the recipient with a dosage of antibodies or antigen-binding fragments which is in the range of from about 1 pg/kg to 10 mg/kg (body weight of mammal), although a lower or higher dosage may be administered. The therapeutically effective dose can be lowered by using combinations of the above described antibodies or antigen binding fragments. As used herein, one compound is said to be additionally administered with a second compound when the administration of the two compounds is in such proximity of time that both compounds can be detected at the same time in the patient's serum.

The antibodies or antigen-binding fragments of the present invention are intended to be provided to recipient subjects in an amount sufficient to lessen or attenuate the severity, extent or duration of the inflammatory symptoms.

The antibody agents of the invention, or their fragments, may be administered either alone or in combination with one or more additional anti-inflammatory or anti-asthma agents (such as catecholamines, resorcinols, salingenins, and ephedrine), glucocorticoids (such as hydrocortisone), chromosomes (such as cromolyn sodium) and anticholinergics (such as atropine), in order to decrease the amount of such agents needed to treat the inflammatory or asthma symptoms.

The administration of the agents of the invention may be for either a "prophylactic" or "therapeutic" purpose. When provided prophylactically, the agents are provided in advance of any symptom. The prophylactic administration of the agents serves to prevent or attenuate any subsequent inflammatory response. When provided therapeutically, the agents are provided at (or shortly after) the onset of a symptom of inflammation. The therapeutic administration of the agents serves to attenuate any actual inflammatory episode. The agents of the present invention may, thus, be provided either prior to the onset of an anticipated inflammatory episode (so as to attenuate the anticipated severity, duration or extent of the episode) or after the initiation of the episode.

The antibodies may be administered by any route appropriate to the condition being treated including intravenous, intraperitoneal, intramuscular, subcutaneous, oral, nasal and the like. Preferably, the antibody is injected into the blood stream of the mammal being treated. It will be readily appreciated by those skilled in the art that the preferred route will vary with the condition being treated.

While it is possible for the antibody to be administered in a pure or substantially pure form, it is preferable to present it as a pharmaceutical formulation or preparation.

The formulations of the present invention, both for veterinary and for human use, comprise an antibody as described above, together with one or more pharmaceutically acceptable carriers and optionally other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method well-known in the pharmaceutical art.

All methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous, subcutaneous, or intraperitoneal administration conveniently comprise sterile aqueous solutions of the active ingredient with solutions which are preferably isotonic with the blood of the recipient. Such formulations may be conveniently prepared by dissolving solid active ingredient in water containing physiologically compatible substances such as sodium chloride (e.g. 0.1–2.0M), glycine, the like, and having a buffered pH compatible with physiological conditions to produce an aqueous solution, and rendering said solution sterile. These may be presented in unit or multi-dose containers, for example, sealed ampoules or vials.

The formulations of the present invention may incorporate a stabilizer. Illustrative stabilizers are polyethylene glycol, proteins, saccharides, amino acids, inorganic acids, and organic acids which may be used either on their own or as admixtures. These stabilizers are preferably incorporated in an amount of 0.11–10,000 parts by weight per part by weight of antibody. If two or more stabilizers are to be used, their total amount is preferably within the range specified above. These stabilizers are used in aqueous solutions at the appropriate concentration and pH. The specific osmotic pressure of such aqueous solutions is generally in the range of 0.1–3.0 osmoles, preferably in the range of 0.8–1.2. The pH of the aqueous solution is adjusted to be within the range of 5.0–9.0, preferably within the range of 6–8. In formulating the therapeutic agent of the present invention, anti-adsorption agent may be used.

Additional pharmaceutical methods may be employed to control the duration of action. Controlled release preparations may be achieved through the use of polymer to complex or absorb antibodies of the present invention or antigen-binding fragments, or their functional derivatives. The controlled delivery may be exercised by selecting appropriate macromolecules (for example polyester, polyamine acids, polyvinyl, pyrrolidone, ethylenevinylacetate, methylcellulose, carboxymethylcellulose, or protamine, sulfate) and the concentration of macromolecules as well as the methods of incorporation in order to control release. Another possible method to control the duration of action by controlled-release preparations is to incorporate the antibodies or antigen-binding fragments, or their functional derivatives, into particles of a polymeric material such as polyesters, polyamine acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

When oral preparations are desired, the compositions may be combined with typical carriers, such as lactose, sucrose, starch, talc magnesium stearate, crystalline cellulose, methyl cellulose, carboxymethyl cellulose, glycerin, sodium alginate or gum arabic among others.

EXAMPLE 1

Production of Hybridomas and Methods For Characterizing the Antibodies

Immunization and monoclonal antibody generation.

Mouse L1-2 lymphoma cells stably expressing human E-selectin cDNA (L1-2ELAM) (Picker et al., 1991 *Cell* 66:921–933, incorporated herein by reference) were used as the immunogen for generation of antibodies of the present invention. Briefly, L1-2ELAM cells ($2 \times 10^7$) were injected i.p. into C57BL/6 mice at bi-weekly intervals (a total of 3 injections) in the absence of adjuvant. The last boost was done 4 days prior to the fusion. The SP2/0 myeloma cell line was used as a fusion partner and previously described procedures were followed in the generation of hybridomas (Kishimoto et al., 1990 *Proc. Natl. Acad. Sci.* USA. 87:224–2248, incorporated herein by reference). The SP2/0-Ag14 myeloma cell line is available from the American Type Culture Collection (ATCC), 12301 Parklawn Drive, Rockville, Md., 20852, USA under Accession No. CRL 1581. The fusion was screened on day 10 by flow cytometry using E-selectin transfected and mock transfected L1-2 cells. A total of 279 wells were screened and 15 selected for further analysis. Secondary screens included SDS-PAGE/ Western blot analysis, immunohistology, and staining of peripheral blood leukocytes. As described below, EL-246, which is a mouse IgG1, was found to stain both E-selectin transfectants and human leukocytes.

Animals.

The animals used as sources of blood (see below) were randomly selected from the large animal facilities at Montana State University. Both Balb/C and C57BL/6 mouse strains were used. The mice ranged in age from 6–12 weeks and were used primarily for the generation of monoclonal antibodies or as source of lymphoid tissues. The mice were housed in the small animal facility at Montana State University which is AAALAC approved. One month old calves, housed in the MSU large animal facility, were used as sources of peripheral blood in some experiments.

Monoclonal antibodies utilized.

Leu-8 (purchased from Becton Dickinson & Co., Mountainview, Calif.) and DREG series of mAb (DREG 56, DREG 200, and DREG 152), which are mouse IgGs that have been shown to recognize human L-selectin (Camerini et al., 1989 Nature (London) 342:78–80; Kishimoto et al., 1990 Proc. Natl. Acad. Sci. USA. 87:2244–2248, incorporated herein by reference) were used in the flow cytometric and Western blot analysis described below. Leu-8 was used as a phycoerythrin (PE) conjugate and the DREG mAb were used as unconjugated mAb followed by appropriate second stage or as fluorescein isothiocyanate (FITC) conjugates. The DREG mAbs were partially purified by ammonium sulphate precipitation. Other mAbs, DREG55 (mouse anti-L-selectin IgG1, SH43 (mouse IgG1 anti-sheep platelet, Jutila M. A. unpublished) and EL-81 (mouse IgG1 anti-ELAM-1), were used as negative controls in many of the experiments described below.

Flow cytometric analysis was performed on a FACScan® (Becton and Dickinson, Mountain View, Calif.) as described (Jutila et al. 1989 Immunol. 143:3318–3324; Kishimoto et al., 1989 Science (Wash. D.C.) 245:1238–124]; Jutila et al., 1990 Cell. Immunol. 132:201–214, incorporated herein by reference). Flow cytometric analysis was performed to verify the specificity of the EL-246 monoclonal antibody for E-selectin and L-selectin as shown by fluorescence of cells expressing E- or L-selectin and negative fluorescence of cells not expressing E- or L-selectin after treatment with EL-246. For two color analysis, PE-conjugated Leu-8 (Becton Dickinson) or a FITC-conjugated DREG Mab were used in combination with EL-246. The cells stained with second stage were treated with 10% mouse serum to block any available anti-mouse Ig binding sites and negative control mouse mAbs were used to evaluate the level of background staining. Data were collected from 10,000–50,000 cells and are presented as histograms or contour plots.

Western blot SDS-PAGE analysis.

Western blot analysis was conducted to verify the specificity of the EL-246 monoclonal antibody for E-selectin and L-selectin using cell lysates from cells expressing E-selectin or L-selectin or immunoaffinity purified E-selectin or L-selectin. Positive staining by the EL-246 antibody of protein bands corresponding to the appropriate molecular weight for E-selectin and L-selectin, was indicative of a specificity for both selectins.

Lysates of human peripheral blood lymphocytes or L1-2ELAM cells suspensions were prepared by incubating $3 \times 10^7$ cells in 1.0 ml of NP-040 lysis buffer (3% NP-40, 150 mM NaCl, 1 mM $MgCl_2$, 5 mM EDTA, 0.02% $NaN_3$, and 10 μg/ml of the following protease inhibitors, pepstatin A, antipain, leupeptin, chymostatin, benzamidine, and PMSF; all in 50 mM Tris-HCL pH 7.5) for 30 min on ice. Lysates were clarified by centrifugation at 10,000 g for 10 min and either used for affinity purification or directly in SDS/PAGE-Western blot analysis.

For affinity isolation, CNBR-activated Sepharose 4B beads (Pharmacia) were coupled to appropriate mAb (4 mg of mAb/ml of beads) according to manufacturer's instructions (Pharmacia Fine Chemicals) using poly preparatory chromatography columns (Bio-Rad Laboratories, Richmond, Calif.). One ml of lysate containing the antigen of interest was mixed with 3 ml of wash buffer (150 mM NaCl, 1 mM $MgCl_2$, 01% NP40, 5 mM $NaN_3$, 20 mM Tris Buffer, pH 7.5), and combined with the beads described above on a rotator for 2 hr at 4° C. After the incubation, the beads were washed with 10 mls of wash buffer to remove any unbound antigen. Bound antigen was eluted with 3 ml of elution buffer (500 mM NaCl, 0.1% NP40, 5 mM $NaN_3$, 200 mM acetic acid) and eluents collected in 0.5 ml fractions and neutralized with 100 μl of 1M Tris buffer, pH 8.0. Fractions containing proteins of interest were determined by Dot-Blot analysis.

For SDS/PAGE-Western blot analysis, crude lysates or affinity purified antigen were mixed with equal volumes of 2x nonreducing SDS-solubilization buffer, run on a 8% SDS-PAGE gel, and transferred to nitrocellulose with a BioRad transblot apparatus per manufacturer's directions (BioRad Laboratories). Mild nondenaturing conditions were used (no boiling and most procedures done at 4° C.). Filters were incubated with 50% horse serum in Tris Balanced Salt Tween TBST (10 mM Tris-HCl, pH 7.4, 150 mM NaCl, and 0.05% Tween-20) for 30 minutes. Using a 25 lane mini-blot apparatus (Immunonetics, Cambridge, Mass.), the filters were then incubated for 30 mins with either specific or negative control mouse mAb at 50 μg/ml concentrations or as culture supernatant fluid. The nitrocellulose filters were then washed in TBST, incubated with goat anti-mouse Ig-alkaline phosphatase conjugate (Sigma Chemical Co., A-9654), diluted 1:200; and then washed again. The blots were developed by addition of substrate solution (Promega Biotech, Madison, Wis.).

Leukocyte cell suspensions.

Leukocytes were harvested from the peripheral blood of humans, goats, sheep, cattle, horses, pigs, rats and chickens. For routine immunofluorescence staining, RBCs (except chicken RBCs) were lysed in a hypotonic solution. Human blood was used as a source of leukocytes for the functional assays described below. Previously described methods were used to isolate both mononuclear cells and neutrophils (Kishimoto et al., 1990 Proc. Natl. Acad. Sci. USA. 87:244–2248; Jutila et al., 1989 Immunol. 143:3318–3324; Kishimoto et al., 1989 Science (Wash. D.C.) 245:1238–1241; Jutila et al., 1990 Cell. Immunol. 132:201–214, incorporated herein by reference). Briefly, blood was collected into citrate anti-coagulant tubes, diluted 1:2 with warm Hanks Balanced Salt Solution (HBSS), underlayed with Histopaque 1077, and centrifuged at 2,300 RPM for 30 min at room temperature. Mononuclear cells were collected from the Histopaque/plasma interface. The pellet, which includes RBCs and neutrophils was resuspended to its original volume in HBSS and the neutrophils isolated by Dextran sedimentation. Residual RBCs in both the mononuclear cell and neutrophil preparations were lysed by hypotonic treatment.

Immunofluorescence staining.

Immunofluorescence staining of leukocytes was carried out as described (Jutila et al., 1989 Immunol. 143:3318–3324; Koshimoto et al., 1989 Science (Wash., D.C.) 245:1238–1241; Jutila et al., 1990 Cell. Immunol. 132:201–214; Stamper et al., 1976 J. Exp. Med. 144:828). Briefly, $1 \times 10^6$ cells were initially incubated in 2% rabbit serum for 10 minutes on ice to block Fc receptors. The cells were washed and then incubated with primary antibody at 50 ug/ml (or undiluted culture supernatant) for 20 minutes on ice. After washing, bound antibodies were revealed by incubation with PE or FITC conjugated F(ab)'2 goat anti-mouse Ig (Tago Inc., Burlingame, Calif.) at a 1:80 dilution in 5% FBS in DMEM.

Immunoperoxidase staining.

Acetone-fixed 6 μm frozen sections of tonsils were incubated with antibodies in phosphate buffered saline (PBS) (50 μg/ml) for 30 minutes at room temperature in a humidified chamber, and then washed in PBS. Using a TAGO histochemical kit (Histoprobe, TAGO, Burlingame, Calif.), a 3 stage immunoperoxidase stain using an avidin biotin system was done per manufacture's instructions. Sections were lightly counterstained with hematoxylin.

In vitro PMA treatment of peripheral blood leukocytes.

Isolated peripheral blood mononuclear cells from the animals listed above were incubated with phorbol myristate acetate (PMA) (10 ng/ml, Sigma, St. Louis, Mo.) for 20 minutes at 37° C. in HBSS. After the incubation period, the cells were washed, and then stained for flow cytometric analysis.

EXAMPLE 2

EL-246 Recognition of Human E-selectin

Figure 2:
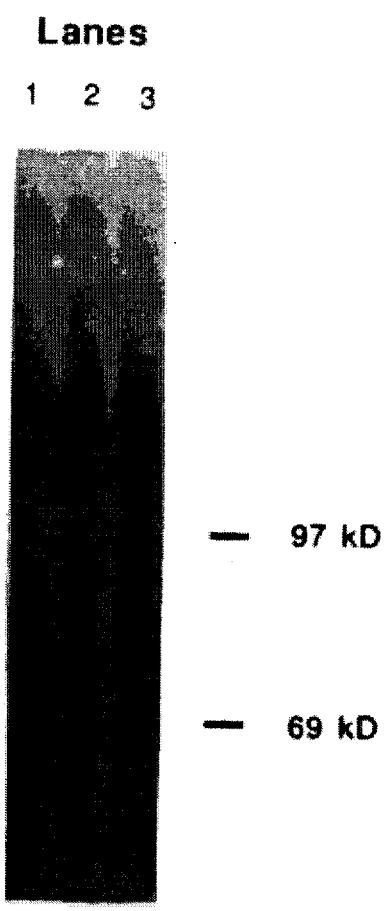
FIG. 2. Shows EL-246 recognition of a 110 kD antigen expressed by L1-2ELAM cells. The blots were probed with EL-81 (anti-E-selectin, lane 3), EL-246 (lane 2), and negative control antibody (lane 1).
Figure 3:
FIG. 3. Shows EL-246 recognition of inflamed venules in frozen sections of human tonsil.

EL-246 was initially screened on human E-selectin cDNA transfected mouse L1-2 cells by flow cytometry and SDS PAGE/Western blot. As shown in FIG. 1, E-selectin transfected, but not the mock transfected L1-2 cells, stained brightly with EL-246 in flow cytometric analysis indicating a specificity of the antibody for E-selectin. The arrows point to histograms which represent (1) EL-246 staining of L1-2ELAM (2) L1-2 transfectant negative controls, and (3) background staining (second stage control) of the L1-2ELAM transfectants. The molecular weight of the antigen expressed by the transfectants recognized by EL-246 was approximately 110kD under nonreducing SDS PAGE/Western blot (FIG. 2) which is the appropriate molecular weight for E-selectin. L11-2ELAM NP40 lysate was run on a nonreducing 8% SDS/PAGE and transferred to nitrocellulose. The blots were probed with EL-81 (anti-E-selectin, lane 3), EL-246 (lane 2), and negative control antibody (lane 1). The distance of migration of the molecular weight markers were as indicated. EL-246 also recognized E-selectin cDNA transfected L-cells, but did not recognize P-selectin cDNA transfected cells as shown by flow cytometry and Western blots. As an additional means of showing the reactivity of EL-246 with E-selectin, sections of inflamed tonsil tissue were stained for immunohistological analysis. As shown in FIG. 3, EL-246 stained venules (E-selectin) in inflamed human tonsil. Frozen sections of human tonsil were prepared as described in Example 1 and stained by immunoperoxidase with EL-246 (Magnification, 400×). Therefore, using accepted biochemical and molecular criteria EL-246 clearly recognized human E-selectin.

EXAMPLE 3

EL-246 Recognition of Human L-selectin

Figure 4A:
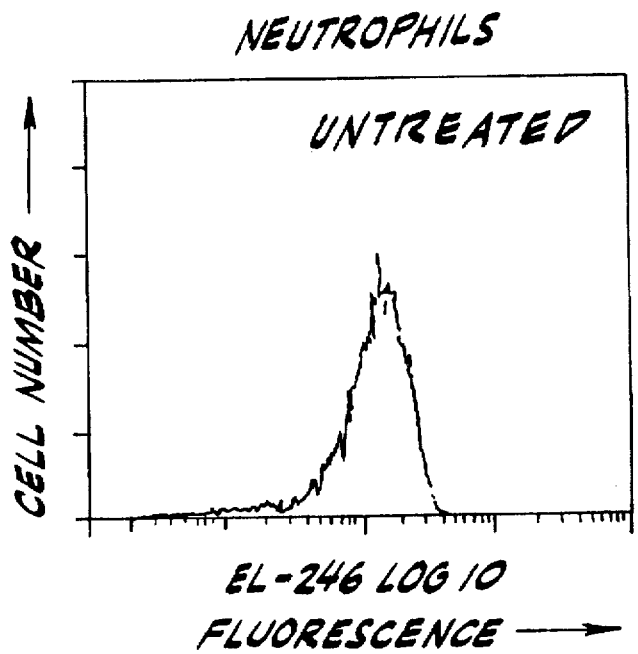
FIGS. 4A–4D. Shows EL-246 recognition of a human peripheral blood leukocyte surface antigen.
Figure 4B:
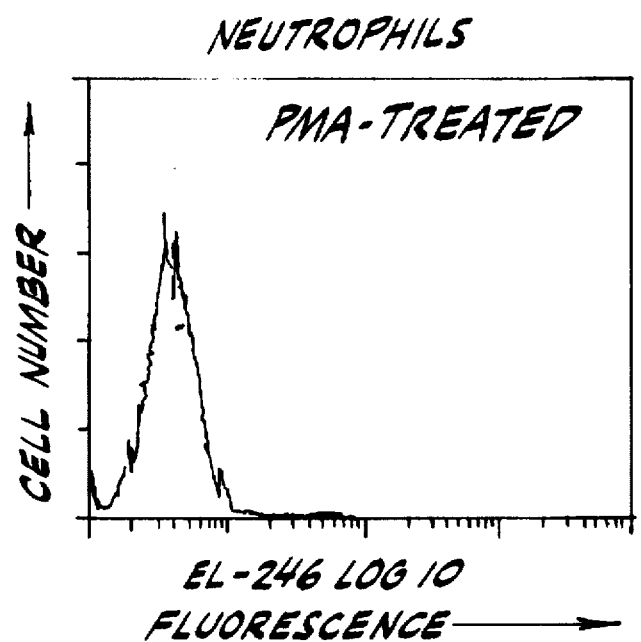
Figure 4C:
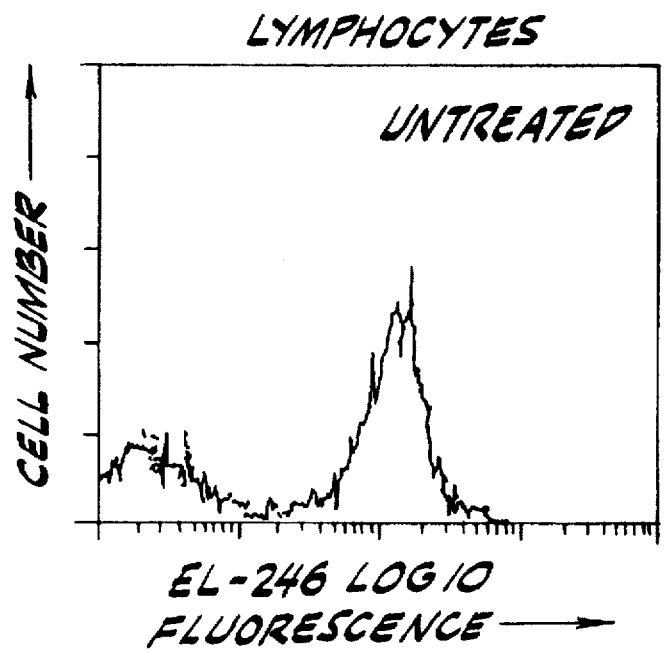
Figure 4D:
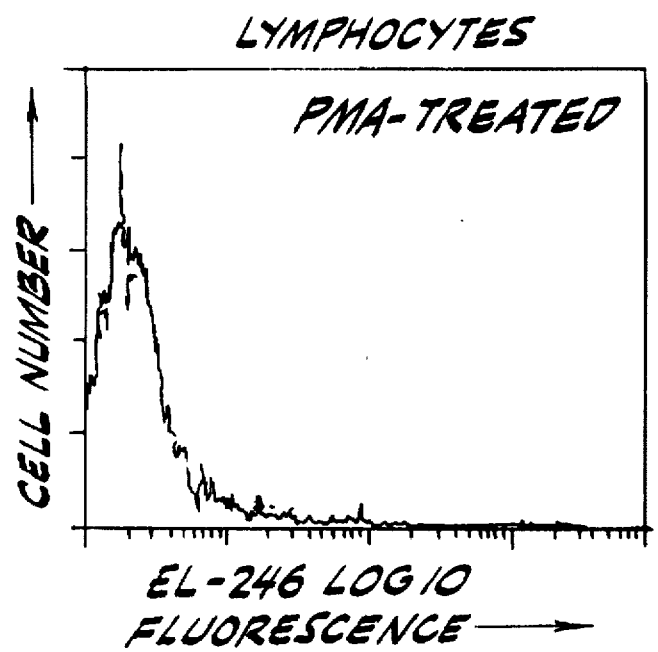
Figure 5:
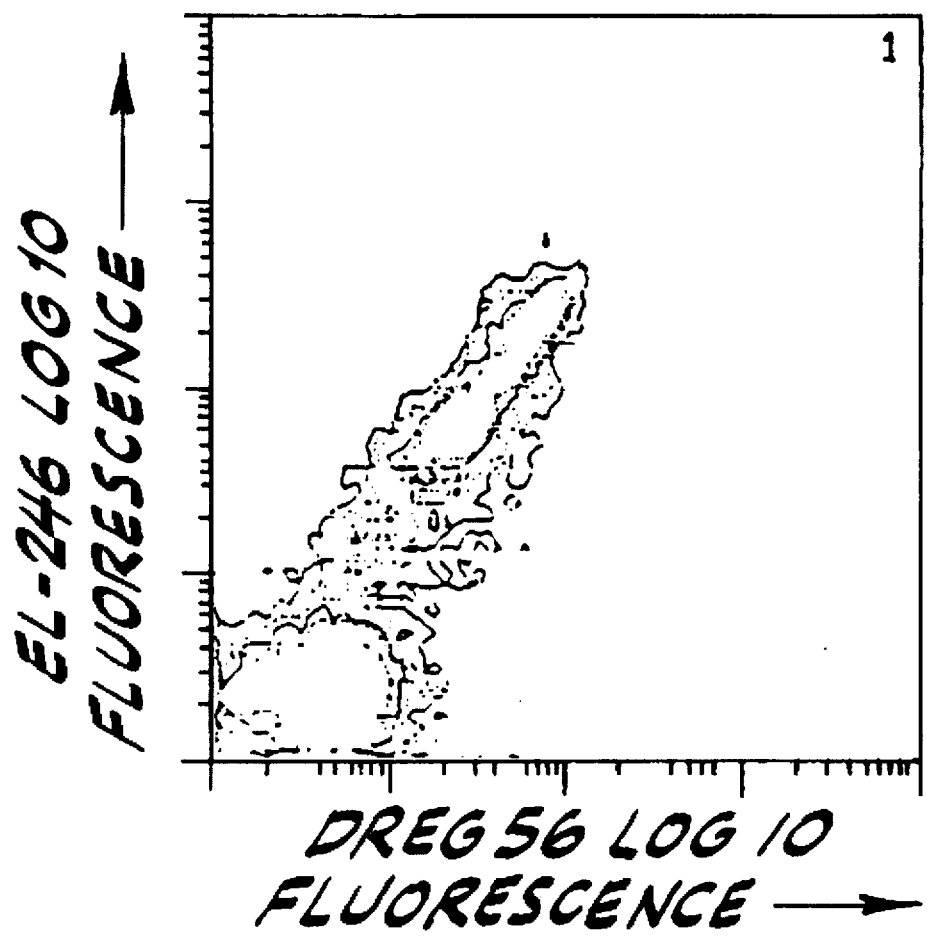
FIG. 5. Shows EL-246 co-staining with anti-L-selectin antibodies.
Figure 6:
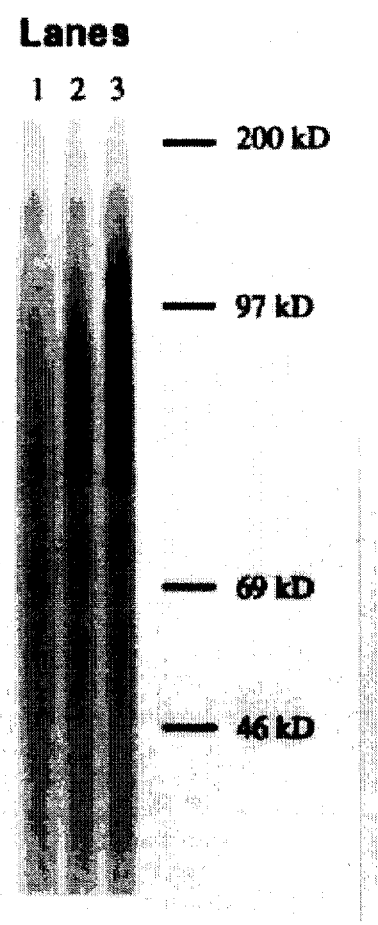
FIG. 6. Shows that EL-246 recognizes affinity purified L-selectin in Western blots. L-selectin was affinity purified using the DREG 56 anti-L-selectin mAb, run on an 8% SDS gel under nonreducing conditions, transferred to nitrocellulose, and probed with EL-246 (Lane 2), another anti-L-selectin in mAb (DREG 152) (Lane 3), or second-stage antibody control (Lane 1).

Flow cytometric analysis showed that EL-246 also stained human peripheral blood leukocytes. The leukocyte surface antigen is down-regulated after treatment with PMA (FIG. 4B and FIG. 4D). Human peripheral blood leukocytes were isolated as described in Example 1 and stained with EL-246 for flow cytometric analysis. The expression of the EL-246 antigen on neutrophils and lymphocytes, which were identified by their distinctive forward and side light scatter profiles, is shown in the representative histograms. A comparison of the staining before (untreated; FIG. 4A) and 20 minutes after PMA activation (PMA-treated; FIG. 4B) is shown. Background fluorescence with an isotype control or second stage alone gave a mode fluorescence value of <10 in each analysis. All circulating human neutrophils expressed the EL-246 antigen, whereas, variable numbers of lymphocytes were positive, which is the same distribution pattern described for L-selectin (Kishimoto et al., 1990 Proc. Natl. Acad. Sci. USA. 87:244–2248; Kansas et al. 1985 J. Immunol. 134:2995). In two color flow cytometry, all EL-246 positive cells were shown to be DREG 56 (anti-L-selectin mAb (Kishimoto, et. 1990 Proc. Natl. Acad. Sci. USA. 87:224–2248) positive and the staining patterns of the two antibodies were similar (FIG. 5). Two color flow cytometric staining was done using FITC-labeled DREG 56 (anti-L-selectin mAb (29) and EL-246 as described in Example 1. A contour plot is shown with demonstrates that all EL-246 cells are also L-selectin positive. The human leukocyte EL-246 antigen was lost from the cell surface after activation of neutrophils and lymphocytes with PMA (FIG. 4B and 4D, respectively), which is also characteristic of L-selectin. Cells transfected with human L-selectin cDNA, but not the transfectant controls, were specifically stained with EL-246 (see below). Finally, the reactivity of EL-246 was also confirmed at the protein level, since immuno-affinity purified L-selectin was recognized by EL-246 mAb in Western blots (FIG. 6-Lane 2). Therefore, by accepted biochemical and molecular criteria EL-246 also reacted with L-selectin.

EXAMPLE 4

The EL-246 Epitope Is Expressed on Selectins From a Variety of Different Animals To evaluate the level of evolutionary conservation of the EL-246 epitope peripheral blood cells from a variety of different animals were screened for EL-246 staining by flow cytometry. As shown in Table 1, EL-246 stained leukocytes isolated from humans, goats, sheep, cattle, and pigs. Chicken and rat leukocytes were EL-246 negative by flow cytometric analysis, which was also confirmed by lack of staining of cytospin preparations. The antigen recognized by EL-246 in these other animals had the characteristic distribution of L-selectin, with lymphocytes exhibiting a bi-modal distribution, and its surface expression lost after the cells were treated with PMA.

TABLE 1

EL-246 recognizes L-selectin in a variety of different animals

| | Reactivity with L-selectin on PBL* | |
|---|---|---|
| Animals | EL-246 mAb | DREG 56 mAb |
| Human | +++ | + |
| Sheep | +++ | – |
| Goats | ++ | – |
| Cattle | +++ | + |
| Pigs | ++ | – |
| Horses | – | – |
| Rats | – | – |
| Chickens | – | – |

*PBL = Peripheral blood lymphocytes

EXAMPLE 5

EL-246 Blocks the Function of Both L-selectin and E-selectin

The ability of EL-246 to block E- and L-selectin function was tested. The function universally attributed to L-selectin is the adhesion of lymphocytes to high endothelial venule (HEV) cells in peripheral lymph nodes (Rosen, 1990 *Am. J. Respir. Cell. Mol. Biol.* 3:397–402; Berg et al., 1989 *Immunol. Rev.* 108:5–18). The Stamper-Woodruff assay is an ex vivo assay that is accepted by those skilled in the art as replicative of adhesive interactions between lymphocytes and the endothelium of lymphoid organs in vivo (Lasky, L. A. 1992 Chapter 3, In: *Adhesion. Its Role In Inflammatory Disease* J. M. Harlam and D Y Liu (eds.) W. H. Freeman and Company, N.Y., pp. 43–63). In this assay, frozen sections of various lymphoid organs are incubated with lymphocytes, the sections washed, and the degree of specific binding between the added lymphocytes and specialized high wall endothelium of the post capillary venules of these organs determined.

Figure 7A:
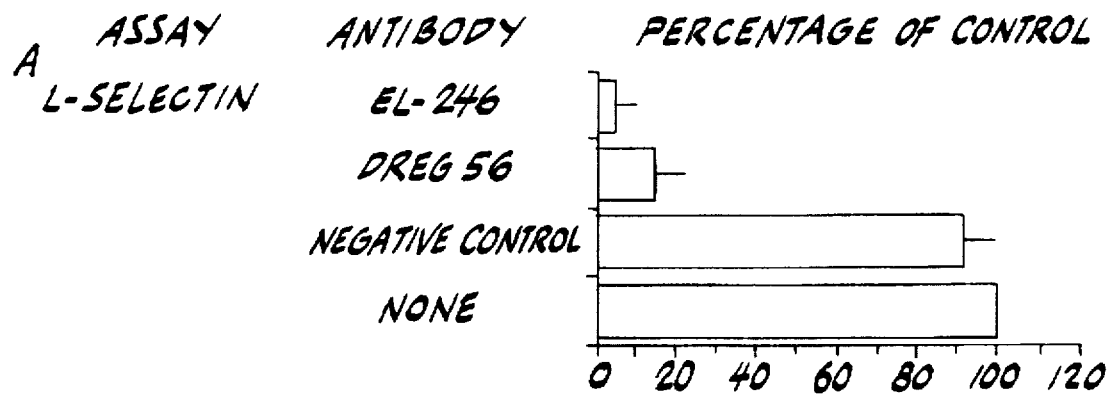
FIG. 7A. Shows EL-246 blocking the function of L-selectin.

Using the Stamper and Woodruff ex vivo frozen section binding assay (Stamper et al. 1976, *J. Exp. Med.* 144:828), it was found that EL-246 blocked lymphocyte adhesion to peripheral lymph node high endothelial venules equally as well or perhaps better than our previous blocking anti-L-selectin mAb, DREG 56 (95.6±4.8% versus 88±5.1% blocking, respectively) (FIG. 7A). Human lymphocytes were treated with EL-246, DREG56, or an isotype matched negative control (EL-81) for 20 minutes on ice and the effect on binding to peripheral lymph node HEV determined. Control mAb, including some generated in the same fusion which yielded EL-246, had no effect on lymphocyte-HEV binding (FIG. 7A). EL-246 did not significantly block the binding of FITC-PPME to human lymphocytes, another function mediated by L-selectin (Rosen, 1990 *Am. J. Respir. Cell. Mol. Bio.* 3:397–402). These results are similar to the blocking activity of mAb directed to the EGF domain of L-selectin (Kansas et al., 1991 *J. Cell. Biol.* 114:351–358; Siegeleman et al., 1989 *Cell* 61:611–622).

Figure 7B:
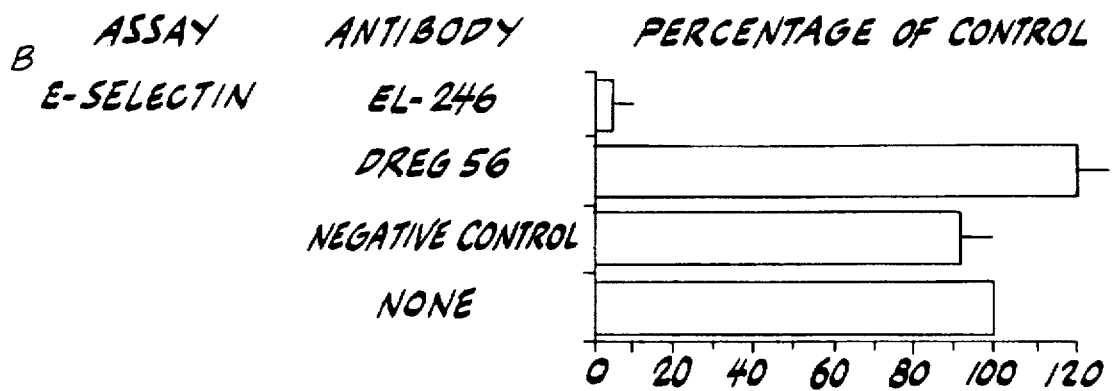
FIG. 7B. Shows EL-246 blocking the function of E-selectin.

To examine the effect of EL-246 on E-selectin function, the ability of neutrophils to bind L-cells stably expressing E-selectin was tested. In this binding assay the adhesion of neutrophils to the transfectants is clearly E-selectin-dependent (Kishimoto et al., 1990 *Blood* 78,805–811). The transfectants were treated with EL-246 for 30 minutes and washed prior to addition of purified human neutrophils. Fc receptors were saturated by pretreating the neutrophils with 10% RBS for 20 minutes prior to the assay. As shown in FIG. 7B, EL-246 nearly completely blocked the binding of neutrophils to the transfectants (90%), whereas another mAb (EL-81) (isotype negative control), which recognizes E-selectin, had little effect on binding. Likewise, treatment of the E-selectin transfectants with an anti-L-selectin specific mAb (DREG 56) also had no effect on binding (FIG. 7B). Values were recorded as percentage of control cell binding, where controls cells were incubated in assay medium alone. The experiments were repeated 3× and the means±sem are presented. Therefore, EL-246 is an effective blocker of E-selectin function.

Neutrophil-E-selectin transfectant binding assay.

L-cells stably expressing human E-selectin cDNA (80% ELAM-1 positive determined by flow cytometry), previously described in Kishimoto et al., 1900 *Blood* 78:805–811, were grown on plastic 8-well Lab Tek slides (Miles Scientific). Neutrophils isolated from human peripheral blood were resuspended at 1×10$^6$ cells/ml in cRPMI, and 400 µl added to the wells of the transfected L-cell cultures. The neutrophils were allowed to adhere at room temperature for 15 minutes under constant rotation, as previously described (Kishimoto et al., 1990 *Blood* 78:805–811). After the incubation, the medium in each well was aspirated, slide chambers removed, and the slides placed in a coplin jar with 1.0% glutaraldehyde in HBSS. Adhesion was measured by counting the number of neutrophils/L-cell. The effect of mAb treatment of the L-cells was determined as follows. In all experiments the neutrophils were pre-coated with 10% rabbit serum to block available Fc binding sites. The E-selectin transfectants were treated with EL-246 (culture supernatant or 50 µg/ml purified antibody), DREG56 or an isotype negative control mAb for 20 minutes on ice, washed, and then used in the adhesion assay.

Peripheral lymph node HEV Assay. The in vitro assay of lymphocyte binding to HEVs in frozen sections (Stamper et al., 1976 *J. Exp. Med.* 144:828) has been extensively described (recently reviewed in Berg et al., 1989 *Immunol, Rev.* 108:5). It has previously been shown that HEV in mouse peripheral lymph nodes bind human lymphocytes well, and this binding is dependent upon L-selectin (Kishimoto et al., 1990 *Proc. Natl. Acad. Sci.* USA. 87:2244–2248). Purified human lymphocytes were incubated with EL-246, a blocking anti-L-selectin mAb (DREG 56), or different isotype controls and the effect on adhesion to peripheral lymph node HEV determined. Cell binding was quantified by first identifying HEVs in each field by their characteristic autofluorescence or unique plump morphology, then counting cells bound to HEV, as described (Kishimoto et al., 1990 *Proc. Natl. Acad. Sci* USA. 87:2244–2248, incorporated herein by reference). Data were calculated as number of cells bound per individually scored HEV. For each data point, 150 HEVs in >3 sections were counted, and represent 4 independent experiments. Values are presented as percentage of medium control.

EXAMPLE 6

Mapping of the EL-246 Epitope to the SCR Domains

Domain mapping of the EL-246 epitope.

The epitope defined by the EL-246 mAb was localized using L-selectin/P-selectin chimeras as described by (Kansas et al., 1991 *J. Cell. Bio.* 114:351–358, incorporated herein by reference). Stable transfectants of the 300.19 mouse pre-B cell line (Alt et al., 1981 *Cell.* 27–381) expressing either native L-selectin; L2P, which contains the lectin domain from L-selectin and the remainder of the protein from P-selectin; or L2P3L, in which only the EGF domain of P-selectin has been substituted for that of L-selectin, were produced as described elsewhere (Kansas et al, manuscript in preparation). 5×10$^5$ cells of each type were incubated on ice for fifteen minutes in 100 µL of culture supernatants or PBS/1% FCS containing diluted ascites of the indicated mAb, washed, and incubated with FITC-conjugated goat anti-mouse Ig (TAGO, Burlingame, Calif.). The cells were then washed and analyzed by flow cytometry on an EPICS Profile (Coulter Immunology, Hialeah, Fla.).

Figure 8:
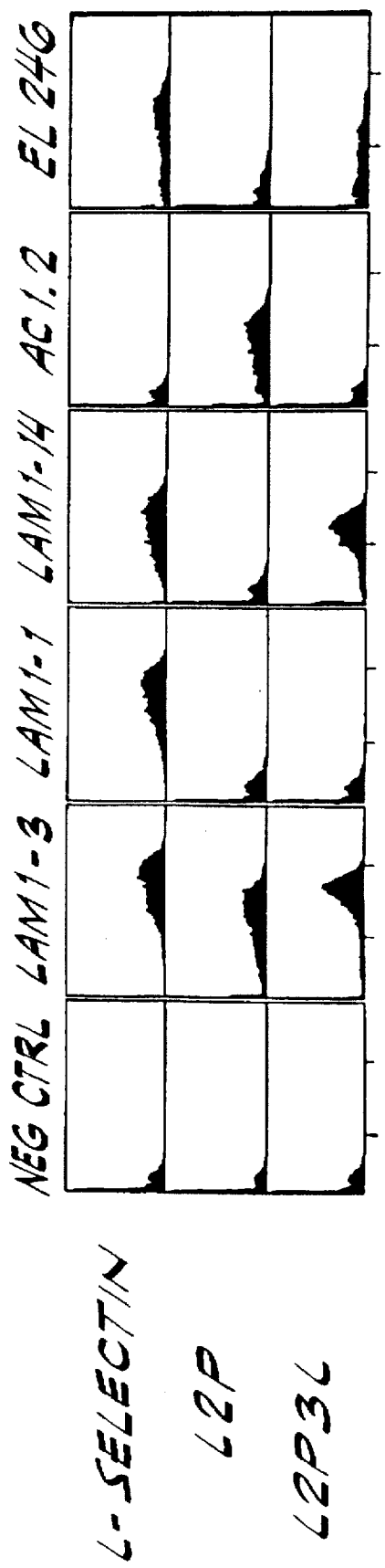
FIG. 8. Indicates that the location of the EL-246 epitope is in or requires the SCR domains of L-selectin.

The pattern of binding of EL-246 mAb to L-selectin/P-selectin chimeras was used to determine the domain of L-selectin in which the EL-246 epitope resides. As controls, the LAM1-3 (Coulter), LAM1-1, and LAM1-14 mAb, which define epitopes within the lectin, EGF and SCR domains of L-selectin, respectively (Kansas et al., 1991 *J. Cell. Biol.* 114:351–358; Spertini et al., 1991 *J. Immunol.* 147:942), and the AC1.2 mAb (Hsu-Lin et al., 1984 *J. Biol. Chem.* 259:9121), which identifies an epitope in the SCR domains of P-selectin (Rosen, 1990 *Am. J. Respir. Cell. Mol. biol.* 3:397–402) were used. El-246 specifically recognized native L-selectin, but not L2P, which contains only the lectin domain from L-selectin (FIG. 8). Analysis was carried out by flow cytometry as described in Example 1. The EL-246 epitope is therefore not within the lectin domain of L-selectin. In addition, EL-246 recognized L2P3L, in which only the EGF domain of L-selectin has been replaced by that of P-selectin. Therefore, EL-246 recognizes only those selectins containing the SCR domains of L-selectin. These date indicate that at least part of the EL-246 epitope is within or requires the SCR domains of L-selectin.

Additional data in support of these results are that EL-246 does not block the lectin activity of L-selectin or cross-block the binding of four mAbs (DREG 200, DREG 55, DREG 56, and Leu-8) that recognize the L-selectin domain.

EXAMPLE 7

Method of Inhibiting L-selectin Dependent Leukocyte Migration

The methods for using antibodies or antigen binding fragments of the present invention for inhibiting L-selectin dependent leukocyte migration is described by Jutila et al., 1989 *J. Immunol.* 143:3318, incorporated herein by reference).

Two methods for demonstrating antibodies in inhibiting inflammatory neutrophil homing in vivo may be used. The first is a modification of the method of Rosen and Gordon (1987 *J. Exp. Med.* 166:1685). Mice are injected i.v. with 500 μg of the various antibodies or saline alone 1 h before the induction of inflammation in the peritoneal cavity with 1 ml of thioglycollate broth. Three hours later, the peritoneal cavities of the mice are washed out with 10 ml of HBSS and the number of newly arrived peritoneal neutrophils are evaluated for each animal. Peripheral blood is also collected from each animal, RBCs are lysed, and the effect of the antibody treatment of circulating neutrophils is quantified. The percentage of neutrophils in the peritoneum and peripheral blood of each animal is determined by FMF analysis after staining with the neutrophil antibody RB6-8C5 and by Wright's stain differentials. FMF analysis is performed on a FACS Star® or FACScan® (Becton Dickinson, Mountain View, Calif.) as described in Jutila et al., 1988 *Eur. J. Immunol.* 18:1819. Antibody blocking data are presented as percent of medium control.

The second approach is the method used by Lewisohn et al. (1987 *J. Immunol.* 138:4313). Bone marrow neutrophils are labeled with FITC (Sigma), as previously described (Butcher et al., *Handbook in Exp. Immunol.* 57.1–57.3), and then 2 to 5×10$^7$ cells are injected i.v. into mice which received 1 to 2 ml of thioglycollate broth i.p. 3 h earlier. The FITC-labeled bone marrow neutrophils localize effectively to sites of inflammation in vivo (Lewinsohn et al., 1987 *J. Immuno.* 138:4313). The cells that accumulate in the inflamed peritoneal cavity are revealed by FMF analysis of 50,000 cells. Data are recorded as the percentage of FITC-labeled donor neutrophils vs unlabeled host neutrophils in the inflamed peritoneal cavity. The unlabeled host neutrophils serve as a standard for the level of inflammation in a given animal. Routinely, the percentage of FITC-labeled neutrophils that accumulate in the inflamed peritoneum ranges from 2 to 8%. For blocking studies, FITC-labeled neutrophils are precoated with the antibodies of the present invention at saturating concentrations for 20 to 30 min on ice. The cells are washed and the are injected into animals that receive thioglycollate 3 h earlier. FMF analysis of 50,000 cells isolated from the peritoneal cavity of each mouse is performed. Clearance of antibody-coated cells is evaluated by examining peripheral blood levels from each test animal. The percentage of FITC-labeled neutrophils vs unlabeled host neutrophils in the peritoneum and the blood of each animal is determined. The data after antibody treatment are presented as a percentage of medium control. The specificity of antibody blocking is determined by calculating a SER for each animal by dividing the percent FITC-labeled neutrophils in the peritoneum by the percent FITC-labeled neutrophils in the peripheral blood. (SER= FITC neutrophils/host neutrophils peritoneal/(FITC neutrophils/host neutrophils) blood. If neutrophil localization at the inflammatory site is blocked due to clearance of the antibody coated cells from the circulation, this results in SER values similar to saline control.

EXAMPLE 8

Method of Screening Antibodies Useful For Prevention and Treatment of Alveolar and Dermal Inflammation The method for demonstrating the effectiveness of the antibodies or antigen binding fragments of the present invention in the prevention or treatment of alveolar and dermal inflammation is described in Mulligan et al. (1991 *J. Clin Invest* 88:1396–1406, incorporated herein by reference).

Monoclonal antibodies.

Antibodies directed against L-selectin and E-selectin are generated as described in Example 1.

The control (non-selectin binding) monoclonal antibody consists of F(ab')$_2$ fragments derived from pepsin digestion. For the immune complex studies of lung and dermal vascular injury, a total of 135 μg antibodies of the present invention or control F(ab')$_2$ are injected intravenously in three equally divided doses at 2.5, 3.0, and 3.5 h after intravenous injection of bovine serum albumin (BSA) and intratracheal instillation or intradermal injection of anti-BSA (which consists of rabbit polyclonal IgG rich in antibody to bovine serum albumin). Negative control animals are not injected with BSA.

Animal models of immune complex alveolitis and dermal vasculitis.

Rabbit polyclonal IgG rich in anti-BSA is used to induce lung and dermal vascular injury (Johnson & Ward, 1981 *J. Immunol.* 126:2365). IgG is purchased from Organon Teknika, West Chester, Pa. The IgG anti-BSA and BSA (Sigma Chemical Co., St. Louis, Mo.) preparations that are used for injection into rats contained 20 pg/ml and 12 pg/ml of endotoxin activity, respectively, as measured by the limulus amebocyte lysate assay (E-toxate, Sigma Chemical Co.). 300–350 g male Long-Evans specific pathogen-free rats (Charles River Breeding Laboratories, Inc., Wilmington, Mass.) are used for all studies. Intraperitoneal ketamine (25–50 mg/100 g body wt) and sodium pentobarbital (5 mg/100 g body wt) are administered for sedation and anesthesia. Immune complex lung injury is induced by the intravenous injection of 100 mg BSA (in 1.0 ml saline) and the intratracheal instillation of anti-BSA in 300 μl. The following intratracheal doses of anti-BSA are used: 0.75 mg, 1.50 mg, 2.50 mg, or 3.33 mg. Rats are killed 4 h after injury and the pulmonary circulation was flushed with 10 ml saline via pulmonary arterial injection. Permeability indices, as a measure of lung injury, are determined by comparing leakages of $^{125}$I-labeled albumin into parenchyma to the amount remaining in 1.0 ml of blood.

Reversed passive dermal Arthus reactions are induced by intradermal injection of 0.10–0.84 mg anti-BSA contained in a volume of 0.10 ml, followed by intravenous injection of 10 mg BSA in 1.0 ml saline. Rats are killed 4 h thereafter and permeability indices calculated by measuring the ratio of radioactivity present in full thickness skin biopsies compared to radioactivity present in 1.0 ml of blood. Negative controls include animals with intradermal sites injected with anti-BSA but with the omission of intravenous injection of BSA.

For assessment of lung or dermal hemorrhage, red blood cells (RBC) are harvested from heparinized blood obtained from normal adult Long-Evans rats. Nine ml of blood is diluted with 40 ml of saline containing 1:1,000 (wt/wt) heparin. To this is added 100 µCi $^{51}$Cr, followed by incubation for 1 h at 37° C. with continuous shaking. After centrifugation at 1,000 rpm (at 4° C.) for 6 min, cells are washed in PBS three times and are then ready for use. Animals are injected with $^{51}$Cr-labeled RBC (45 µL containing 80,000. CCiD) ½ h before injection of BSA and anti-BSA. At the time of killing, skin sites and saline-perfused lungs are measured for $^{51}$Cr radioactivity and compared to counts present in 1.0 ml. of blood. At the conclusion of each experiment, blood samples from each animal are centrifuged and radioactivity measured in the cells and serum. The same injury and treatment protocols are used as described above for immune complex-induced lung and skin injury.

Glycogen-inducedperitoneal exudates.

Neutrophil-rich exudates are elicited in rat peritoneal cavities with the injection of 25 ml 0.1% (wt/vol) oyster glycogen 4 h before killing. 135 µg F(ab')$_2$ fragments of the present invention are injected intravenously in three equally divided doses in the treatment group (at 2.5, 3.0, and 3.5 h) to assess effects on neutrophil recruitment into peritoneal cavities.

Tissue myeloperoxidase (MPO) content.

A standard reference curve is first established by measuring MPO in lungs and skin sites that have been injected with known numbers of neutrophils. Lung and skin sites are extracted by homogenization and sonication procedures that have been previously described (Warren et al., 1989 *J. Clin. Invest.* 84: 1873). MPO activity in supernatants is measured by the change of optical density (at 460 nm) resulting form decomposition at H$_2$O$_2$ in the presence of o-dianisidine.

Immunohistochemical analysis of cells and lung tissue.

Monolayers of rat pulmonary artery endothelial cells (RPAEC) on plastic sides are stimulated with 50 ng/ml human recombinant TNFA for 4 h, washed with PBS, and fixed with acetone. Slides containing monolayers of stimulated and unstimulated cells are then incubated with antibodies of the present invention (1.0 ng/ml) for 45 min. The slides are then washed with PBS and then stained for bound mAb using biotin/avidin-peroxidase system for mouse IgG (Vectastain; Vector Laboratories, Inc., Bulingame, Calif.). After hematoxylin counterstaining, sections are coated with aqua-mount (Lerner Laboratories, Pittsburgh, Pa.) and are examined by light microscopy for the presence of reaction products of peroxidase. Immune complex-induced lung injury is accomplished using the same protocols described above. Animals are killed at 0, 1, 2, 3, and 4 h. The lungs are inflated with 8–9 ml of optimal cutting temperature (OCT) compound (Miles Laboratories Inc., Elkhart, Ind.) and frozen sections obtained from lungs of normal rats and those undergoing intraalveolar deposition of immune complexes. After mounting on poly-L-lysine coated slides and fixation with acetone, tissue sections are then reacted with antibodies of the present invention, as described above.

To assess whether TNF a-stimulated HUVEC (human umbilical vein endothelial cells) removes antibody reactivity, an additional experiment is also carried out using the same staining procedure, and using lung from the 4 h immune complex reaction. Before use, the mAb preparation of the present invention (1.0 ng/ml) is incubated for 1 h at 27° C. with monolayers (5×10$^6$ cells) of TNF α-(50 ng/ml)-stimulated or unstimulated HUVEC, preceding application of antibody to the lung sections.

Morphologic evaluation of lungs and skin.

Lungs are fixed in 10% phosphate buffered formalin for subsequent hematoxylin and esosin staining and examination by light microscopy. Skin samples are similarly treated.

Neutrophil-mediated cytotoxicity of endothelial cells.

Neutrophil-mediated cytotoxicity of RPAEC is measured by a standard $^{51}$Cr release assay (Varani et al., 1985 *Lab. Invest.* 53:656). RPAEC are seeded into wells of a 24-well culture dish, with 5×10$^4$ cells per well in 1 ml culture medium. Each well receives 2 µCi of Na $^{51}$CrO$_4$ (New England Nuclear, Boston, Mass.) and the monolayers are then incubated for 14 h. TNFA is then added at a concentration of 50 ng/ml and the monolayers are incubated for an additional 4 h. The plates are then washed twice with HBSS (Hank's balanced salt solution) containing 0.02% BSA to remove the non-incorporated radioactivity. The endothelial cell monolayers are then ready for use. When antibodies are employed, they are added to the monolayers and are incubated for 30 min. Human blood neutrophils are isolated and suspended in HBSS supplemented with 0.02% BSA. After incubation with Ab, neutrophils are then added to duplicate wells to give effector to target cell ratios of 30:1 in a final volume of 1.0 ml. Neutrophils are allowed to settle onto the endothelial cell monolayers for 30 min before the addition of phorbol myristate acetate (PMA) (50 ng/ml) which is added in a volume of 0.1 ml per well. After an additional incubation of 37° C. for 6 h, 0.9 ml supernatant is removed from each well and any cells in suspensions removed by centrifugation. The supernatant fluid (0.5 ml) is aspirated and assayed in a γ-scintillation counter to determine $^{51}$Cr release.

EXAMPLE 9

Method For Prevention and Treatment of Asthma

The method for demonstrating the effectiveness of the antibodies or antigen binding fragments of the present invention in the treatment of asthma is described in U.S. Ser. No. 738.633 and in Gundel et al., 1991 *J. Clin. Invest.* 88:1407–1411, both incorporated herein by reference.

Animals:

The animals are wild-caught adult male cynomolgus monkeys (*Macaca fascicularis*) weighing approximately 4 to 8 kg (Charles River Breeding Laboratories, Inc., Primate Imports, Port Washington, N.Y.).

Monoclonal Antibody:

Stock solutions of antibodies are diluted with saline (final concentration 2 mg/ml) immediately before intravenous injections into a peripheral leg vein. Antibodies or antigen binding fragment treatment are administered 1 hour before antigen inhalation challenge. Antibody specific for ELAM-1 alone, may be used as a positive control. Antibody against ELAM-1 (CL2) was generated as described in Picker et al., *Nature* 349:796 (1991).

Rrs Measurements:

Respiratory system impedance (Rrs) is measured by discrete frequency (4–40 Hz in 11 equal logarithmic steps)

sinusoidal forced oscillations superimposed on tidal breathing as described in Wegner et al., 1984 *Respir. Physiol.* 55:47. The mean of the real or in-phase component of Rrs over the entire frequency is then computed to provided a single value representation of Rrs.

Bronchoalveolar lavage (BAL):

BAL is performed by guiding a fiberoptic bronchoscope (Olympus Optical, model 3C-10, Lake Success, N.Y.) past the carina and is wedged into a $5^{th}$ to $7^{th}$ generation bronchus. A 15 ml aliquot of bicarbonate buffered saline (pH 7.4, 23° C.) is infused and gently aspirated through a channel in the bronchoscope. Collected samples are centrifuged at 2000 RPM for 10 minutes and the resulting cell pellets are resuspended in $Ca^{++}$ and $Mg^{++}$ free Hank's balanced salt solution. It has been shown that the BAL procedure will elicit a mild inflammatory response. Thus, to avoid the possible effects of BAL on lung cellular composition, BAL is performed alternating the right and left lungs before and after antigen challenge. The return volume of infused buffer is very constant throughout the study and the procedure is well tolerated by the animals. Total white cell counts are obtained using a Coulter counter (Coulter Electronics, model #10, Hialeah, Fla.).

Antigen Inhalation Challenge:

Antigen inhalation challenges are administered by intermittent positive pressure breathing with a Bird 7A respirator and micronebulizer (Bird Corporation, model #8158). Each challenge consisted of 15 breaths per minute (maximum inspiratory pressure of 20 $cmH_2O$) for 2 minutes. *Ascaris summ* extract (Greer Laboratories, Lenoir, N.C.) is diluted with phosphate buffered saline (PBS, pH 7.4) to the appropriate concentration for each animal (dose required to cause a 200–500% increase in Rrs during the immediate response). Antigen challenges are separated by 14 days for each animal. Each animal is fasted for 18 hours prior to the day of study.

Histochemistry:

BAL cells are evaluated using cytocentrifuge preparations stained with DIff-Quick stain (Fisher Scientific, St. Louis, Mo.). Differential cell counts are determined by counting 200 cells and the percentage of each cell type is recorded.

Histology:

Lung biopsy samples are obtained prior to antigen challenge and during the peak late-phase response with biopsy forceps and the fiberoptic bronchoscope. Immunohistochemical staining for identification of E- or L-selectin on pulmonary vascular endothelium and airway epithelium are performed as described in Wegner et al., 1990 *Science* 247:456.

Statistical Analysis:

Data are analyzed statistically using two-way analysis of variance and Friedman's multiple range test.

Study Protocol:

Each animal is anesthetized with an intramuscular injection of ketamine (4 mg/kg; Ketaset, Myoderm Medical Supply, Norristown, Pa.) and xylazine (1 mg/kg/ Rompun, Miles Laboratories, Inc., Naperville, Ill.) intubated with a cuffed endotracheal tube and placed in the supine position. Ketamine (4 mg/kg, i.m.) is used as supplemental anesthesia as needed. Each animal then receives a bolus intravenous injection of monoclonal antibody or vehicle (saline). Airway cellular composition is then evaluated by performing broncoalveolar lavage (BAL) with a pediatric fiberoptic bronchoscope after which the animals are seated in the upright position in a specially designed support chair. Baseline respiratory system resistance (Rrs) is monitored for approximately 15 minutes followed by an inhaled antigen challenge (1 hr. post i.v. treatment). Rrs is monitored continuously for 1 hour after which the animals are allowed to recover from anesthesia and returned to their cages. Rrs is monitored over a 15 minute time period, at 4, 6, 8 and 10 hours after antigen inhalation. Following a recovery period, the late-phase response is assessed by performing BAL (opposite lung lavaged prior to antigen challenge).

The study is designed such that bracketing control experiments (vehicle treatment) are performed on each animal such that each animal serves as its own control. Each study is separated by 14 days.

Pretreatment with antibodies or antigen binding fragments of the present invention 1 hour before antigen inhalation significantly attenuates both the total leukocyte infiltration and the number of infiltrating neutrophils in all animals. Treatment with antibodies or antigen binding fragments for the present invention results in a significant reduction in late-phase bronchoconstriction but has no apparent effect on the acute response.

EXAMPLE 10

Method for Detecting L- and E-selectin Bearing Cells in Biological Samples

Biologicals.

A membrane-bound adhesion molecules can be genetically engineered by those skilled in the art based on the nucleotide sequence (Marlin et al 1990 *Nature* 344:70–72, incorporated herein by reference). The complete nucleotide sequence for E-selectin (Bevilacqua et al., 1989 *Science* 243:1160–1165, incorporated herein by reference) and L-selectin (Bowen et al., 1989, *J. Cell Biol.* 109:421–427; Siegelman et al., 1989 *Proc. Nat'l Acad. Sci.* USA, 86: 5562–5566; Tedder et al., *J. Exp. Med.* 170:123–133, incorporated herein by reference) are reported in the literature. The sequence containing the coding sequence plus the transmembrane and cytoplasmic domains can be amplified by PCR, as described in Mullis U.S. Pat. No. 4,683,195. The gene for E- or L-selectin is subcloned into one of the many available eucaryotic or procaryotic expression vectors and expressed in an appropriate host cell line.

For use as standards in immunoassays such as ELISA Western Blot, and Dot-Blot, known amounts of L-selectin and E-selectin bearing cells or cell lysates are serially diluted in Dulbecco's Phosphate Buffered Saline (DPBS) containing 1% BSA (BSA-DPBS).

Monoclonal antibody preparation.

Mouse anti-L/E selectin antibodies are prepared as previously described in Example 1.

Preparation of test samples.

Human peripheral blood from a test animal is collected in heparinized vials, and PBMC (peripheral blood mononuclear cells) are isolated by using Ficoll-Paque (Pharmacia, Uppsala, Sweden). Thrice-washed PBMC are then resuspended in complete medium as a 5% cell suspension. Two milliliters of the cell suspension are added to appropriate wells of a 24-well flat-bottom plates. At appropriate times, wells from each donor are collected. The cell supernate is centrifuged for 5 min at 5600 x g to remove any particulates and the cell supernate is frozen at 20° C. until all samples are collected for analysis by ELISA. The supernates are thawed, cleared by centrifugation at 10,000 x g for 5 min, and then concentrated eight-fold on Centricon 30 devices as per the manufacturers instructions (Amicon, Beverley, Mass.). The concentrated samples are then immediately assayed for E- or L-selectin by ELISA.

ELISA for L-selectin and E-selectin bearing cells.

Antibody of the present invention in DPBS is added to 96 well flat bottom EIA microliter plates (Linbro) at 50 μl/well at room temperature for 1 h. Wells are washed three times with DPBS and then are blocked with 200 μl of 2% BSA-DPBS for 1 h at 37° C. Wells are flicked empty and a titration of L-selectin & E-selectin standards (twofold serial dilutions, 8–1024 ng/ml) and test samples, suspected of containing L- and/or E-selectin bearing cells, (diluted in 1% BSA-DPBS) are added (50 μl/well) in triplicate for 1 h at 37° C. Wells are washed three times with DPBS. The biotinylated anti L/E-selectin (EL-246) mAb is added at 2 μg/ml (50 μl/well) for 30 min at 37° C. Wells are washed three times with DPBS. An aliquot of 50 μl/well of horseradish peroxidase streptavidin (1:4000) (Zymed, San Francisco, Calif.) is added for 30 min at 37° C. Wells are washed three times with DPBS and once with ABTS substrate buffer (Zymed). ABTS substrate buffer is added (50 μl/well) and the plates are read on a Dynatech Microliter ELISA reader (410 nm) until maximum OD reading are obtained. Mean OD readings are calculated.

EXAMPLE 11

Immunoaffinity Purification of L- and E-selectin Bearing Cells

The present invention can be useful in combination with gene therapy techniques known in the art in the treatment of genetic disease, CD11/CD18 deficiency. The leukocytes with lack functional CD11 and CD18 genes, bear the cell surface receptor, L-selectin and/or E-selectin. The mAbs of the present invention are bound to a solid support which is used as an affinity column. The affinity column specifically binds L-selectin and/or E-selectin bearing cells from a source such as patient's blood thus allowing for their purification or separation from other cells. Such cells, once purified, undergo gene therapy with a DNA vector carrying the CD11 and CD18 genes, and then are re-infused into the patient, thereby establishing a functioning adhesion pathway.

EXAMPLE 12

EL-246 Treatment of Neutrophils Alone Blocks Their Ability to Bind E-selectin cDNA Transfectants.

Figure 9:
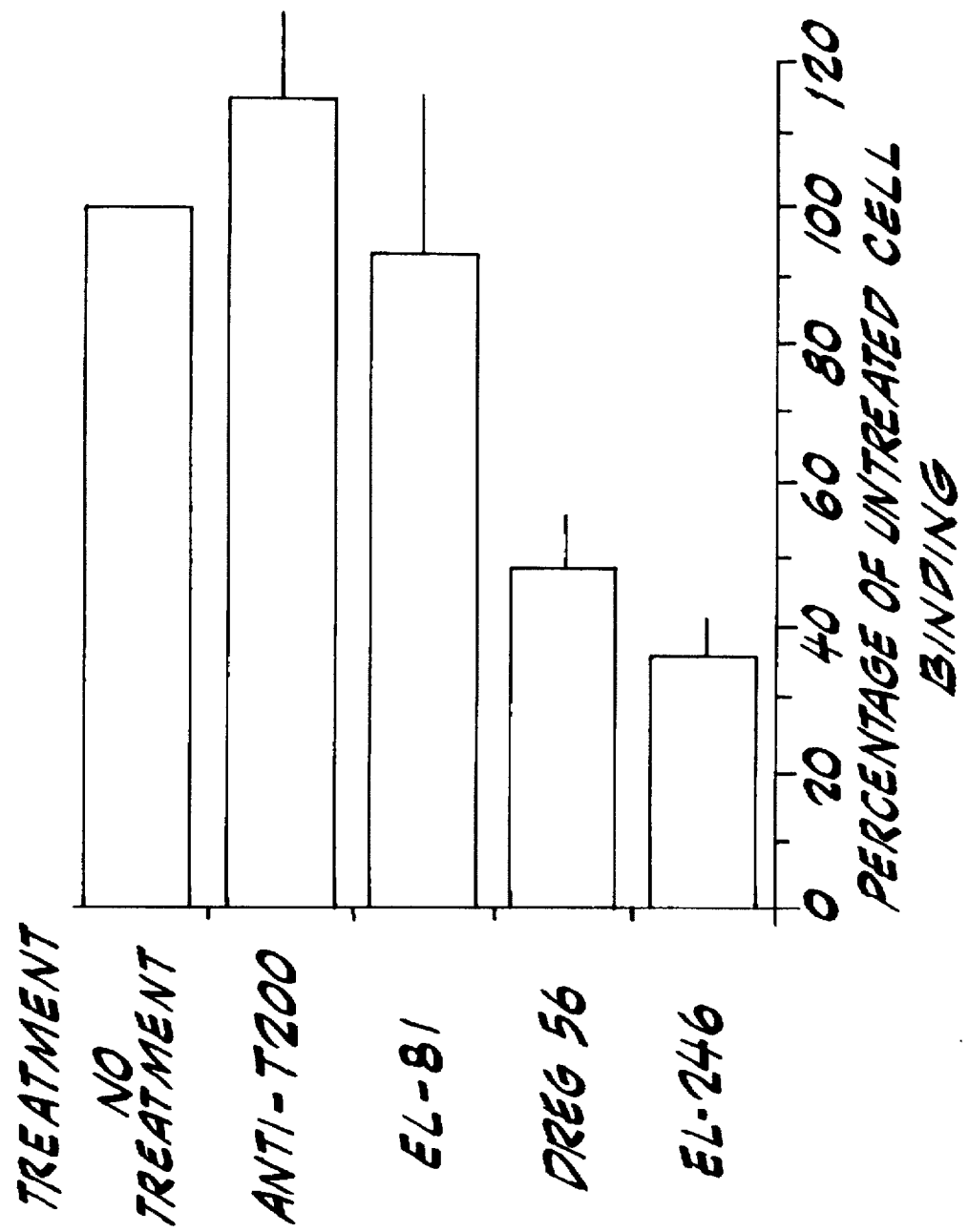
FIG. 9. EL-246 treatment of neutrophils prevents neutrophil binding to E-selectin transfectants (TF).

Pretreatment of E-selectin cDNA transfected fibroblasts with EL-246 blocks the ability of the transfectants to bind neutrophils. Since endothelial cell E-selectin and neutrophil L-selectin may potentially serve as receptor-counter-receptor pairs (Kishimoto, T K et al. 1990. *Blood* 78:805; Picker L J 1991 *Cell* 66:921), inhibition of neutrophil binding to E-selectin was examined by only treating the neutrophil. Peripheral blood neutrophils were incubated with saturating levels of E-246 on ice for 20 min, washed, and then added to cultures of mouse L-cells transfected with human E-selectin cDNA. The effect of EL-246 on binding was evaluated and compared with an anti-L-selectin mAb (DREG 56) and 2 isotype negative control mAbs, anti-T200 and EL-81 which stain leukocyte and E-selectin, respectively. Neutrophils were treated with the indicated antibodies at 50 ug/ml concentrations for 20 min on ice, washed, and then added to the E-selectin transfectants. The binding assay was done as described. The effect of the antibody treatments were quantified and recorded as percent of control (untreated) cell binding. Values represent means±s.d. of 8 values from 2 separate experiments. As shown in FIG. 9, EL-246 blocked adhesion by 64%, DREG 56 inhibited by 53%, and the negative control mAbs had little effect. These results show that EL-246 treatment of neutrophils blocks their ability to bind E-selectin transfectants.

Figure 10A:
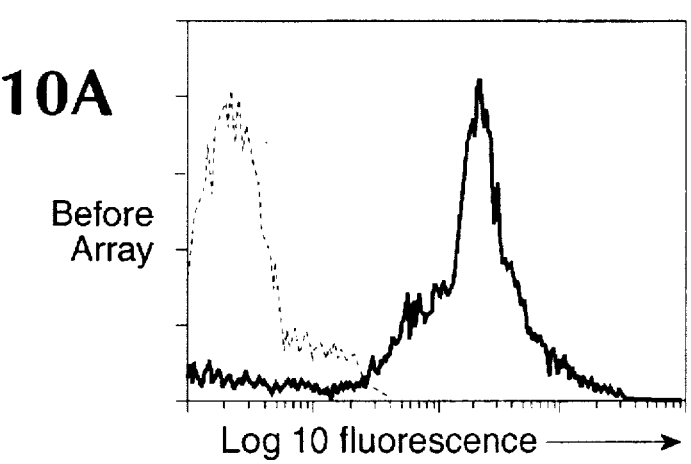
FIGS. 10A through 10F. EL-246 transfers from the neutrophil to the E-selectin transfectants during the binding assay.
Figure 10B:
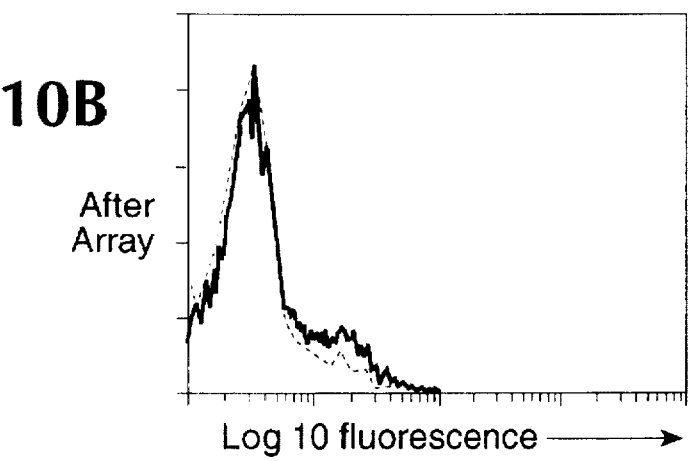
Figure 10C:
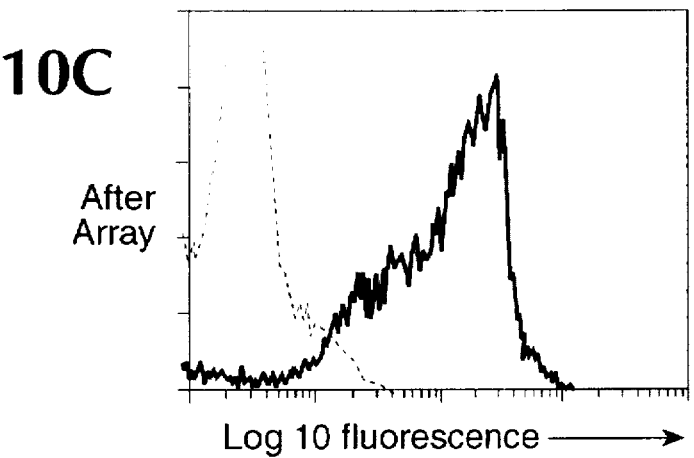

Tests were conducted to determine whether EL-246 could be found on the surface of the E-selectin transfectants after the binding assay by addition of FITC-labeled anti-mouse second stage antibody to the cells, followed by flow cytometric analysis. The neutrophils used in the experiments were pretreated with EL-246, washed and then were analyzed for the presence of EL-246 on their cell surface before and after the assay by addition of FITC-labeled anti-mouse Ig second stage antibody followed by flow cytometry. The E-selectin transfectants were similarly analyzed. The level of EL-246 on the surface of the neutrophil before and after the assay was compared. The neutrophils were saturated with EL-246 at the beginning of the assay (FIG. 10A), however, no antibody could be detected on their cell surface after a 15 min co-incubation with the E-selectin transfectants (FIG. 10B). Since L-selectin can be shed from the surface of leukocytes (Kishimoto, T. K. et al. 1989 *Science* 245:1238), tests were conducted to determine whether the loss of EL-246 antibody on the neutrophil during the binding assay was due to shedding of the molecule. Neutrophils that no longer had EL-246 on their cell surface after the assay (FIG. 10B) stained brightly with a second anti-L-selectin mAb (DREG56) that recognizes an epitope distinct from the one bound by EL-246 (FIG. 10C). This indicates that shedding of L-selectin had not occurred on the EL-246 treated neutrophils.

Figure 10D:
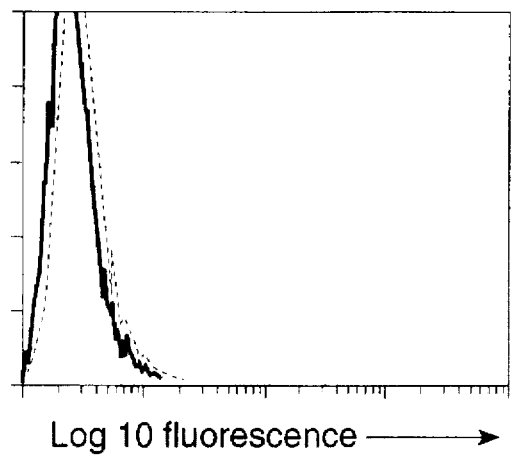
Figure 10E:
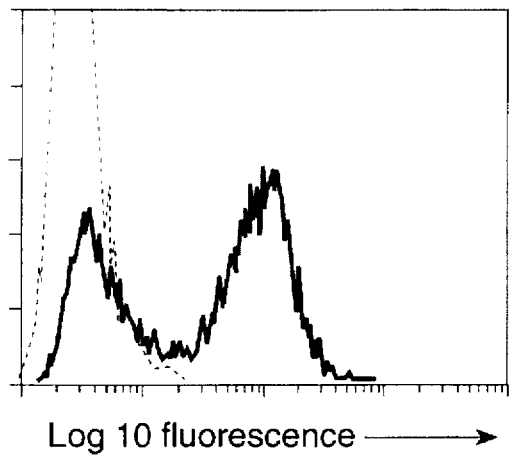
Figure 10F:
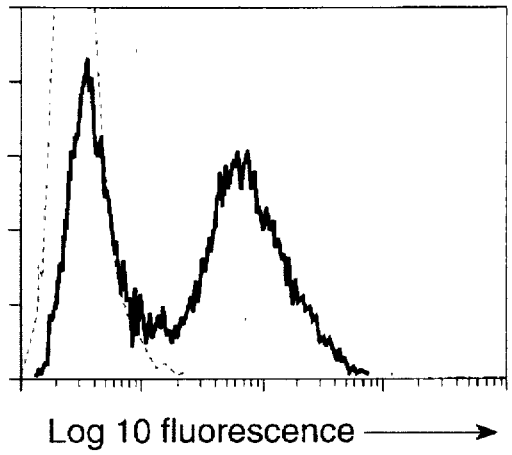

In contrast to the lack of EL-246 on neutrophils after the assay, high levels of EL-246 were detected on the surface of the E-selectin transfectants (FIG. 10E). Transfectants that did not receive EL-246-treated neutrophils did not react with the second stage (FIG. 10D). The level of fluorescence intensity of the transfectants exposed to EL-246 treated neutrophils, followed by second stage antibody (FIG. 10E), was the same or slightly higher than the level of fluorescence obtained after a conventional indirect stain of the E-selectin transfectants using EL-246 (FIG. 10F). These results showed that when neutrophils are pre-treated with EL-246, the mAb apparently has the capacity to transfer from the neutrophil to E-selectin on the L-cell transfectants. Similar results with endothelial cell E-selectin were obtained. Here, human umbilical cord endothelial cells were treated with 10 units/ml TNF for 4 hours to induce E-selectin expression. Neutrophils pretreated with EL-246 were added to the endothelial cells as described above. Within 15 minutes, all neutrophils lost EL-246 which could then be found on the surface of the cytokine-activated endothelial cells. This, EL-246 blocking of neutrophil binding to E-selectin was likely at the level of E- and not L-selectin. Furthermore, these results suggest that neutrophils may efficiently deliver EL-246 to sites of E-selectin expression.

EXAMPLE 13

EL-246 Blocks Neutrophil "Rolling" on Activated Human Umbilical-cord Endothelial Cells (HUVECs)

Selectins are involved in recruitment of neutrophils and other leukocytes to sites of inflammation. The recruitment of neutrophils to sites of inflammation can be divided into three steps: 1) initial attachment and "rolling" of cells on activated endothelium of postcapillary venules; 2) activation of neutrophils and firm adhesion to the endothelium; and 3) extravasation of the cells into the surrounding tissue (Paulson, J. C. 1992 Chapter 2, In: *Adhesion Its Role In Inflammatory Disease*, J. M. Harlan and D. Y. Liu (eds.) W. H. Freeman and Company, New York, N.Y., pp. 19–42). Selectins participate in the initial adhesion or "rolling" of neutrophils on the activated endothelium. Anti-adhesion therapy prevents or inhibits this damage.

Leukocyte traffic across the vessel wall to extravascular vascular tissue is necessary for host defense against microbial organisms or foreign antigens and repair of tissue damage. Under some circumstances, however, leukocyte-endothelial interactions may have deleterious consequences for the host. During the process of adherence and transendothelial migration, leukocytes may release products that directly damage endothelium, cause endothelial dysfunction and tissue damage. (Harlan, J. M. et al. 1992 Chapter 6. In.: *Adhesion. Its Role In Inflammatory Disease*, ibid pp. 117–150). Anti-adhesion therapy prevents or inhibits this damage.

An in vitro flow cells system that mimics in vivo shear force of blood flow in post capillary venules and neutrophils rolling, was used to determine the ability of EL-246 to inhibit neutrophil rolling on an activated endothelial cell layer.

Freshly isolated human umbilical-cord endothelial cells, which were Factor VIII and LDL-receptor positive, were grown to confluency on the internal surface of sterile glass 1.36 mm capillary tubes (Drummond Scientific, Broomall, Pa.). Four hrs prior to the assay, the endothelial cells were treated with 10 ng/ml PMA or lug IL-1 (IL-1 beta, Immunex, Seattle, Wash.) which induces maximal E-selectin expression. Tubing was attached to each end of the capillary tube to form a closed system in which fluid and cells could be recirculated using a variable peristaltic pump. The capillary tube was mounted on the stage of an inverted microscope modified for video microscopy. Purified human neutrophils were injected into the system at a 1×10$^7$ cell/ml concentration in DMEM plus 2% FBS. A reproducible rolling interaction, which did not occur on nonactivated endothelial cells, was detected under a flow rate of 10.1 mm/sec. The rolling interaction was allowed to occur for 5 min while being videotaped, and then EL-246 or an isotype negative control antibody at 50 ug/ml or both were sequentially injected into the system. The leukocyte-endothelial cell interactions were then videotaped for up to 10 min. The number of neutrophils rolling on the activated endothelial cells at 10–30 sec intervals before and after the injection of mAb was determined by analysis of each frame of the videotape recording. Data were recorded as the number of rolling cells within the field of view versus time (seconds).

EL-246 was tested to determine whether it could inhibit the ability of activated endothelial cells to support neutrophil rolling. HUVECs were grown on the internal surface of sterile glass capillary tubes and induced to express E-selectin (confirmed by EL-246 staining), as described. The tubes were set up in a system which measures leukocyte interactions with ligands under conditions of shear. The in vitro loop assay was used to analyze the effect of EL-246 on the capacity of neutrophils to roll on activated endothelial cells as described. A rolling interaction was established and then EL-246 was injected into the system. The number of rolling neutrophils within the microscopic field of observation was quantified over time by analysis of individual frames from the videotape recording of the interaction.

Figure 11A:
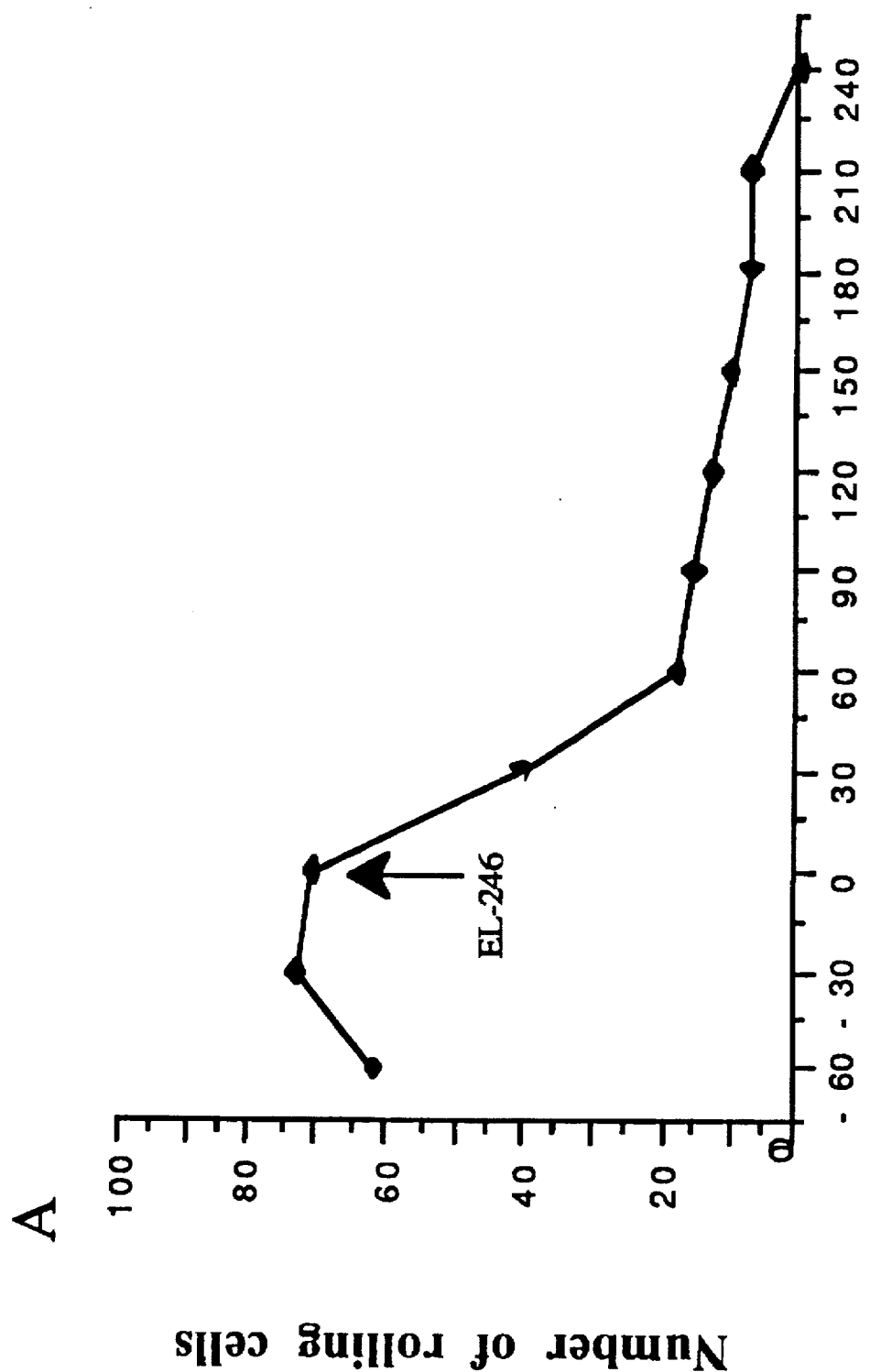
FIGS. 11A through 11B. EL-246 blocks neutrophil rolling on activated endothelial cells under conditions of shear. 11A shows the effect of EL-246 on neutrophil rolling. 11B shows the effect of an isotype negative control mAb on neutrophil rolling.

Under controlled shear conditions, activated HUVECs were quite effective at supporting human and mouse neutrophil rolling (data not shown). To test the effect of EL-246, a rolling interaction between isolated human neutrophils was established and then EL-246 (50 ug/ml final concentration) was injected into the closed loop system, and the effect on neutrophil rolling recorded by videomicroscopy for 10 min. The number of neutrophils rolling on the endothelial cells was determined before and after the injection of EL-246 by analyzing individual frames of the videotape. FIG. 11 A shows a plot of the number of cells rolling on the activated endothelial cells versus time. Within 90 seconds after the injection of EL-246, greater then 75% of the rolling interaction was blocked, and by 4 min the blocking was 100%. In tubes injected with medium alone, no inhibitory effect on the neutrophil rolling was detected. Furthermore antibodies to CD44 and P-selectin had no inhibitory effect in this assay (data not shown).

Figure 11B:
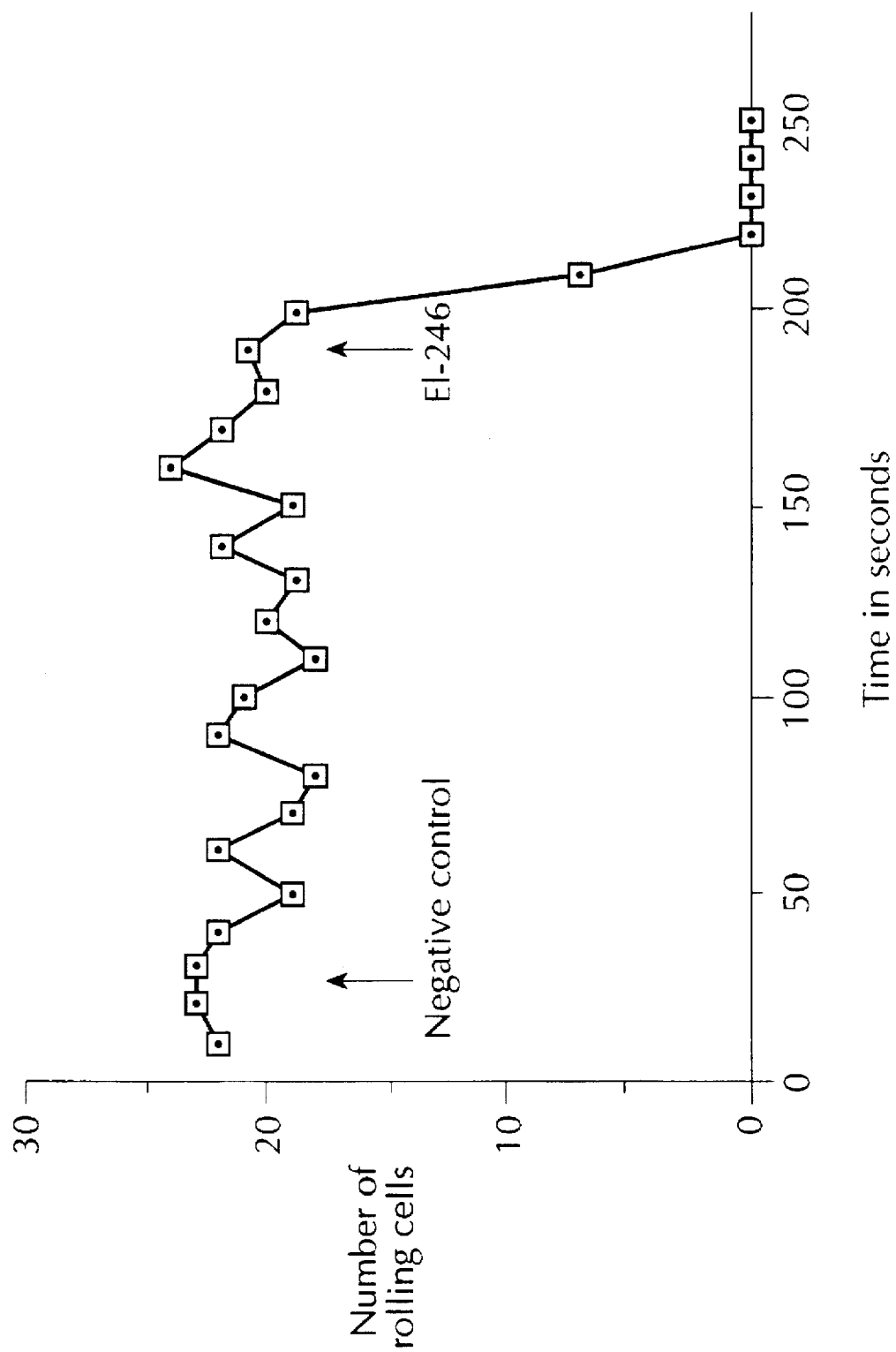

A second type of experiment was done to control for nonspecific effects of mAb on neutrophil rolling within the same tube eventually injected with EL-246. A rolling interaction was established as above and then an isotype negative control mAb (12.2, which does not recognize neutrophils or endothelium) was injected into the system (50 ug/ml) and its effect monitored for 150 sec. As shown in FIG. 11B, 12.2 did not alter the rolling interaction. After 180 sec, EL-246 was injected into the system, which blocked rolling completely (FIG. 11B). In some tubes, the lack of effect of the negative control mAb was seen for over 20 min (data not shown).

The results of these experiments demonstrate that EL-246 monoclonal antibody is unique in its ability to inhibit neutrophil rolling on activated endothelium and supports its use in vivo for inhibiting neutrophil rolling for prevention or inhibition of leukocyte migration and inflammation.

EXAMPLE 14

EL-246 Blocks the Ability of E-selectin CDNA Transfectants to Bind Peripheral Lymph-node HEV Peripheral lymph node HEV binding Assay.

The in vitro assay of lymphocyte binding to HEVs in frozen sections and the mouse pre-B L ½ cells transfected with E-selectin cDNA or vector cDNA were the same as used in Example 5. Mouse L ½ cells expressing functional human E-selectin and the nontransfected control parent line were resuspended in cRPMI at 1×10$^7$ cells/ml and 100 ul added to 10 um sections of mouse peripheral lymph node, and the HEV binding assessed. Cell binding was quantified by first identifying HEVs in each field by their characteristic autofluorescence or unique plump morphology and then counting cells bound to HEV, as described in Example 5. After the assay, the sections were stained with thionin which preferentially labels the binding cells a dark blue. Data were calculated as number of cells bound per individually scored HEV. The effect of antibody treatment on the transfectants was compared to medium alone.

Figure 12A:
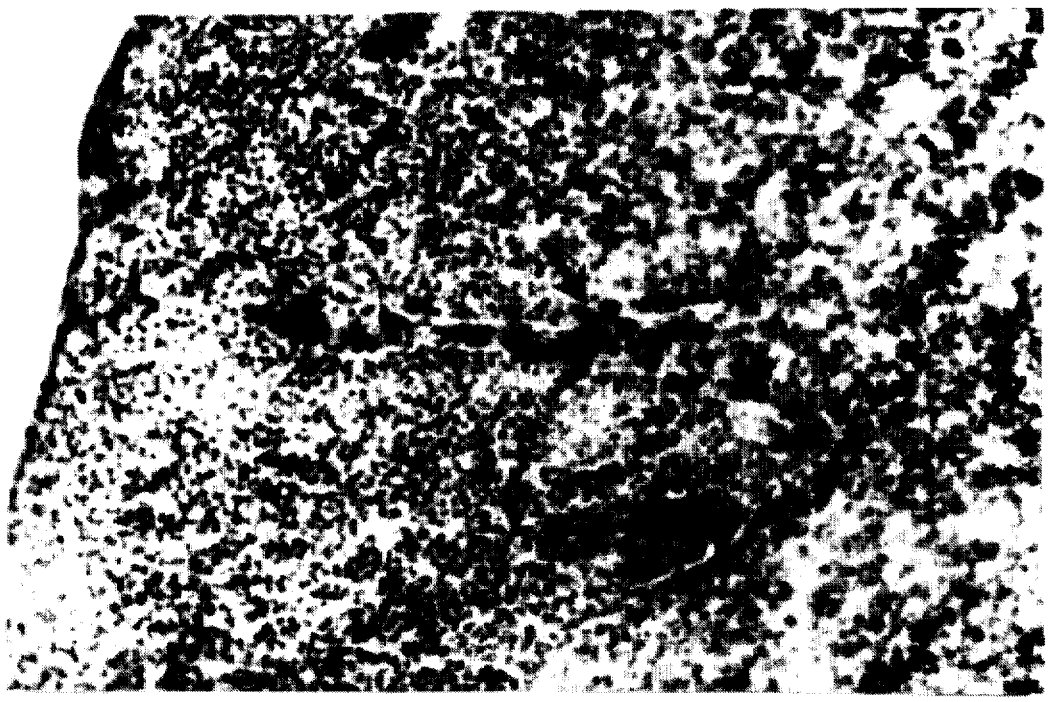
FIGS. 12A through 12B. EL-246 blocks the binding of E-selectin transfectants to peripheral lymph node HEV.
Figure 12B:
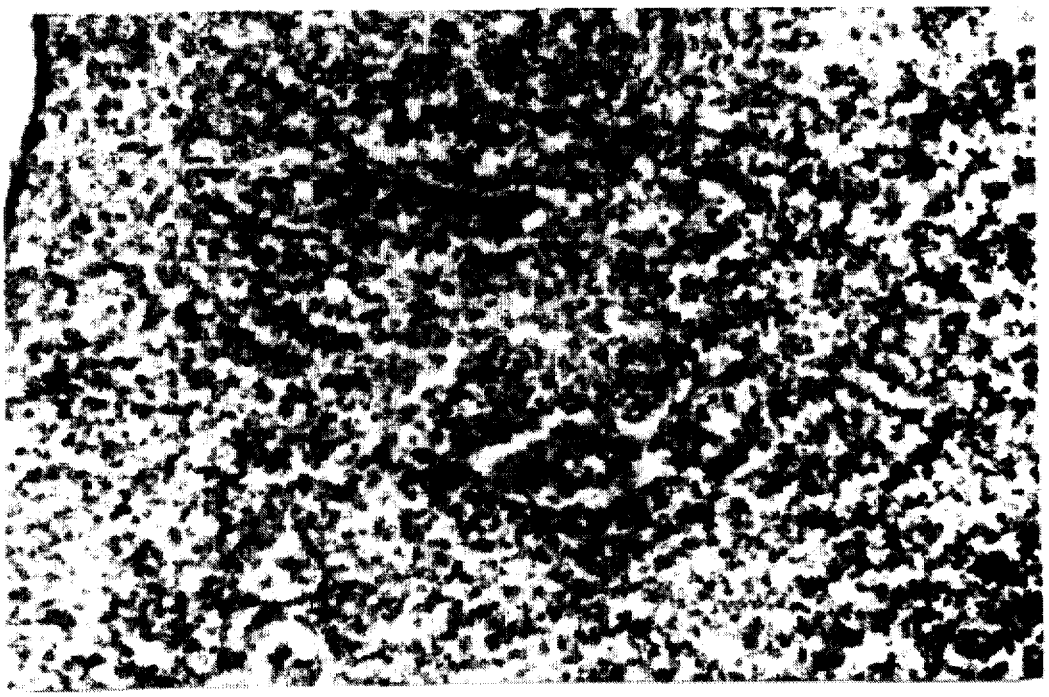
Figure 13A:
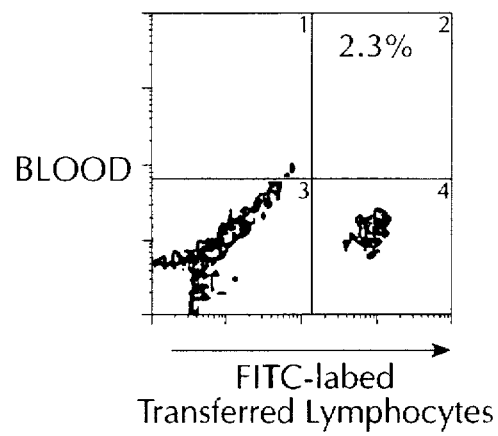
FIG. 13A through 13B. EL-246 specifically blocks the ability of bovine lymphocytes to home to mouse peripheral lymph nodes. The contour plots represent the analyses of the percentage of FITC-labeled bovine lymphocytes that homed into blood spleen and peripheral lymph nodes (PLN) following treatment (trtd.) with EL-246 (FIGS. 13G through 13I), DREG 55 (FIGS. 13D through 13F) or medium alone (FIGS. 13A through 13C) (control).
Figure 13B:
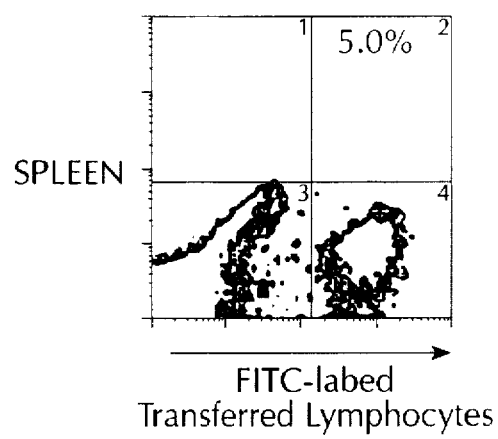
Figure 13C:
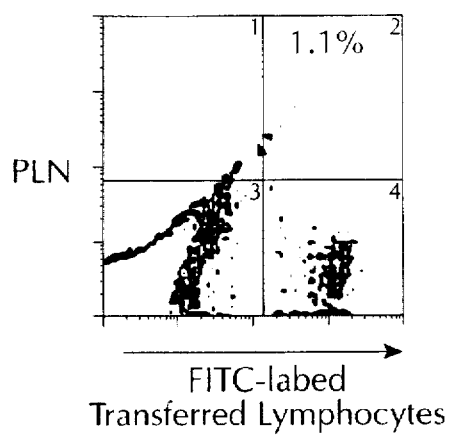
Figure 13D:
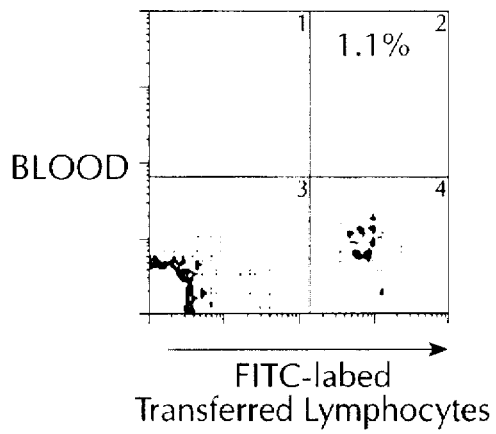
Figure 13E:
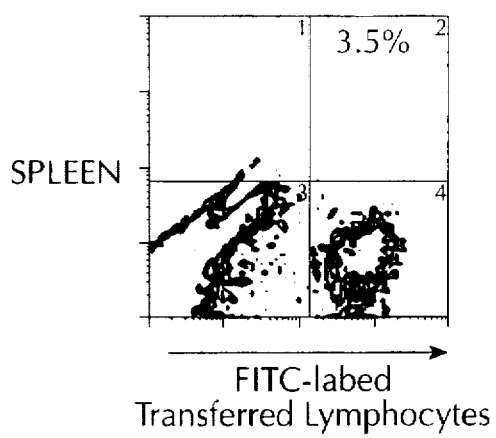
Figure 13F:
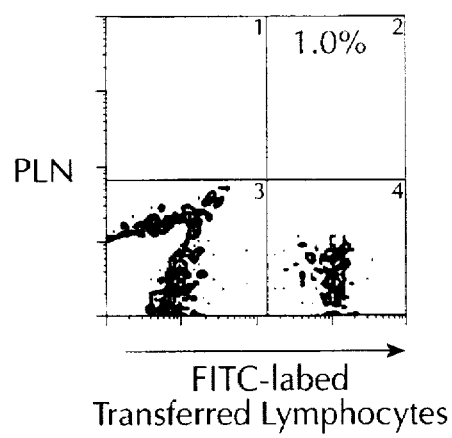
Figure 13G:
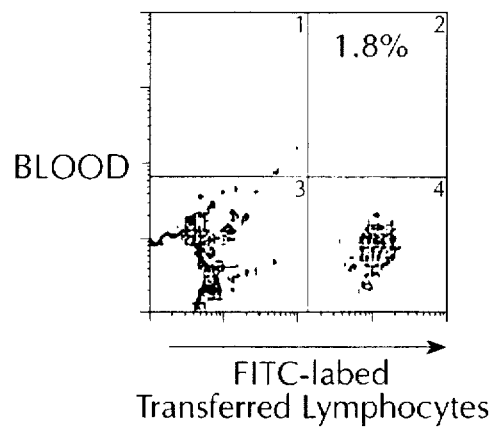
Figure 13H:
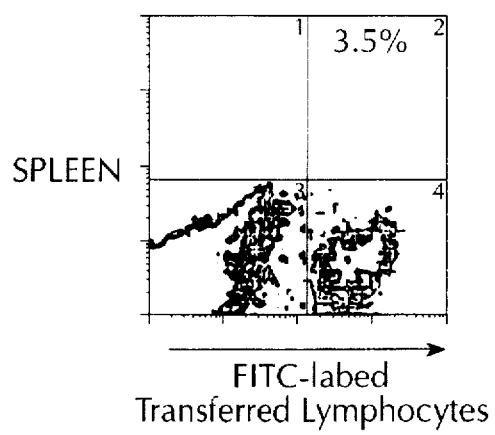
Figure 13I:
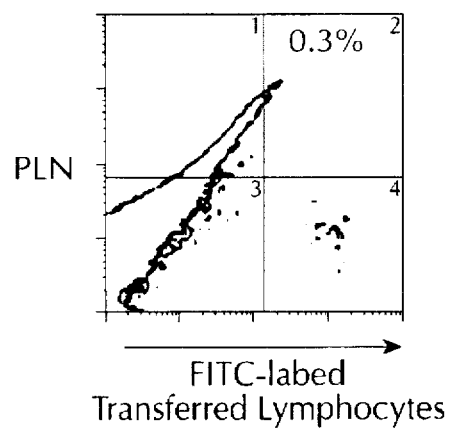

Berg E. L., Robinson, M., and colleagues have shown that there are overlapping binding specificities between L- and E-selectin (Berg, E. L. et al. 1992 *Biochem. Biophys. Res. Comm.* 184:1048). Both molecules bind the same carbohydrates and, interestingly, E-selectin transfectants avidly adhere to peripheral lymph-node HEV (Berg et al., ibid) a molecular interaction originally thought to be unique for L-selectin (Butcher, E. C. 1991 *Cell* 67:1033). EL-246 was tested to determine if it blocked the interaction of the E-selectin transfectants with PLN HEV. As shown in the photomicrographs of FIG. 12A, the mouse L ½ lymphoma cell line, transfected with human E-selectin cDNA, avidly bound to mouse PLN HEV. EL-246 treatment of the transfectants completely blocked this interaction (FIG. 12B). This experiment was repeated 4 times, and in each experiment the blocking of EL-246 was 100%.

EXAMPLE 15

EL-246 Blocks the Homing of Lymphocytes into Peripheral Lymph Nodes In Vivo Xenogeneic lymphocyte in vivo homing assay.

Bovine lymphocytes were isolated from peripheral blood, washed, suspended at $1\times10^7$ cells/ml in HB101 (NEN), and labeled with FITC as described (Jutila, M. A. et al. 1989, *J. Immunol.* 143:3318; Jutila, M A 1990 *Cell Immunol.* 132:201, incorporated herein by reference). These procedures led to 100% efficiency in homogeneously labelling all of the lymphocytes with resulting mode fluorescence values ranging from 100–500. The FITC-labeled lymphocytes were washed in HBSS, resuspended at $1\times10^8$ cells/ml and 0.5 ml of the cell preparation injected into the lateral tail vein of 6–12 week old, female BALB/c mice. After 4 hrs, the animals were sacrificed and Peyer's patches (PP), mesenteric lymph nodes (MLN), peripheral lymph nodes (PLN), spleen, and peripheral blood were collected. Single cell preparations were made from each tissue. RBCs in the peripheral blood were lysed by hypotonic lysis, and then flow cytometric analysis was done to quantify the capacity of the transferred lymphocytes to enter lymphoid tissues of the mouse, as previously described (Jutila, M. A. 1990 *Cell. Immunol.* 132:201). The percentage of transferred versus host lymphocytes was determined for each tissue. The effect of antibody on the homing of the lymphocytes was compared to medium controls. Additional controls in this assay were 1) quantifying blood levels to show that clearance of the antibody treated cells did not occur, and 2) the tissue specific effects of EL-246. L-selectin preferentially mediates lymphocyte homing through peripheral lymph nodes. To achieve optimal results, the donor animals had to be healthy and less than 1 mo old (the age when L-selectin is expressed at its highest level on the greatest percentage of circulating lymphocytes). Furthermore, cell separation and labeling techniques could not take more than 2 hrs, otherwise there was a drop in cell viability. Assays were not included for analysis if xenogeneic lymphocyte homing in control animals (at least 0.2% of host peripheral lymph node lymphocytes, for example) did not occur.

The xenogeneic homing model was used to test whether EL-246 was effective at blocking lymphocyte homing into peripheral lymph nodes in vivo—another selectin-mediated function. Xenogeneic lymphocytes home with appropriate specificity to lymphoid tissues of mice in short-term homing assays (Bargatze, R. and Jutila, M. A., unpublished observations). This is not surprising since the primary adhesion pathways required for homing are highly conserved in mammals (Jutila, M. A. et al. 1992 *J. Exp. Med.* 175:1565; Spertini, O. et al. 1991 *J. Immunol.* 147:942; Wu, N W 1988 *J. Cell. Biol.* 107:1845; Walcheck, B. et al. 1992 *Eur. J. Immunol.* 22:469). The assay is completed within 4 hrs; thus, few complications related to xenogeneic responses are detected. This approach provides a powerful system to measure the homing capacity of lymphocytes from large animals in which homologous homing experiments are difficult due to the large numbers of cells required. Bovine lymphocyte homing in the mouse was examined because 1) EL-246 recognizes bovine L-selectin, 2) large numbers of cells can be easily obtained, and 3) healthy young animals (1 mo), in which virtually all circulating lymphocytes are L-selectin positive (as any animal matures the percentage of L-selectin positive lymphocyte drops), can be readily used.

MEL-246 or medium-alone-treated, FITC-labeled bovine lymphocytes were injected into identical mice and allowed to home for 4 hours. After the incubation, the animals were sacrificed and blood and various lymphoid organs collected. The percentage of FITC-labeled cells compared to unlabeled host cells was determined for each tissue and compared between the various treatments. Table 2 shows the combined data from 7 different experiments (except for the Peyer's patch which was analyzed 3 times).

TABLE 2

EL-246 pretreatment of bovine lymphocytes blocks their ability to home to peripheral lymph nodes of the mouse.

| Tissue | Percentage of host cells[a] | | Percent blocking[b] | |
|---|---|---|---|---|
|  | Control | EL-246 | | |
| PLN | 0.4 ± 0.14 | 0.14 ± 0.05 | (P, 0.10) | 65% (n = 7) |
| MLN | 0.48 ± 0.22 | 0.24 ± 0.08 |  | 50% (n = 7) |
| PP | 0.45 ± 0.24 | 0.34 ± 0.03 |  | 25% (n = 3) |
| Spleen | 1.54 ± 0.63 | 1.30 ± 0.50 |  | 15% (n = 7) |
| Blood | 0.66 ± 0.32 | 1.10 ± 0.55 | No reduction | (n = 7) |

[a]Values represent the percentage of FITC-labeled cells in 50,000 cells analyzed from each tissue and are means ± SEM from the number of experiments indicated.
[b]Percent blocking by EL-246 calculated as follows: 100 (100 × percentage of cells in tissues following EL-246 treatment/percentage of cells in tissues of controls). Controls were cells treated with medium alone and then injected into the mice.

The percentage of FITC-labeled control lymphocytes found in the peripheral lymph node ranged from 0.2%–1.6%. As expected, there was variability (indicated by high SEM) in the level of homing between experiments which likely was due to variability in cell preparations, animals, and/or other factors. Even with this variation the pooled data from control and EL-246 peripheral lymph nodes were significantly different (65% inhibition, P value 0.10). If the percent inhibition within each experiment was calculated and averaged, far less variation was seen (64%±10 SEM, significant at a P value<0.01). Blocking was also seen in all of the other tissues tested, but was only slightly significant in the mesenteric lymph node (P value 0.30). The reduced homing after EL-246 treatment was not due to increased clearance of the treated cells from the circulation, since blood levels were the same in the two treatment groups (Table 2).

The effect of a negative control antibody (DREG55) was examined. This antibody is the same isotype and was prepared in the same manner as EL-246 but does not recognize bovine lymphocytes. The xenogeneic lymphocyte in vivo homing assay was done as described in Table 2, and the effects of EL-246 and a negative control antibody (DREG55 same isotype as EL-246, but does not recognize bovine lymphocytes) were evaluated by flow cytometry. The contour plots shown in FIG. 13 represent the analyses of this experiment and report the percentage of FITC-labeled bovine lymphocytes that homed into spleen and PLN following treatment with EL-246, DREG 55, or medium alone (control). 50,000 cells were analyzed for each time point and the threshold for the contour levels were the same in each plot. The quadrants were based on the upper limit of background fluorescence.

FIG. 13 shows representative flow cytometric contour plots of the data collected from animals injected with medium alone, DREG55, and EL-246-treated, FITC-labeled cells. Again, EL-246 blocked homing to the peripheral lymph node and slightly diminished accumulation in the spleen. DREG55 had no effect on the accumulation of cells in the PLN; however it affected accumulation in the spleen to the same extent as EL-246. Importantly, EL-246 blocked homing to PLN by 70% in comparison to the effect of DREG55, even though there were 2 times the level of circulating EL-246-treated versus DREG55-treated cells in the test animals. These results show that EL-246 is an effective inhibitor of L-selectin in this in vivo model.

EXAMPLE 16

Treatment of Ischemia/Reperfusion

EL-246 ameliorates or inhibits Ischemia/Reperfusion injury in vivo.

Ewes of approximately 24–30 Kg weight were used in the experiments. The accepted lung ischemia/reperfusion model was followed as described by Kapelanski, D. P. et al. 1993 *J. Heart Lung Transplant.* 12:294-306, incorporated herein by reference. Briefly, general anesthesia was induced in the ewes with this pental sodium and maintained by continuous administration of fentanyl citrate. Complete paralysis was sustained by continuous administration of pancuronium bromide.

Volume-controlled ventilation (tidal volume, 600 ml; fraction of inspired oxygen, 0.53; inspiratory:expiratory ratio, 1:1 positive end-expiratory pressure 5.0 cm $H_2O$) (608 ventilator; Harvard Apparatus, INc., S. Natick, Mass.; air-oxygen mixer; Sechrist Industries, Inc., Anaheim, Calif.; positive end-expiratory pressure valve; Boehringer Laboratories, Inc., Norristown, Pa.) was delivered through an 8-mm cuffed endotracheal tube. The ventilator rate (10 to 15/min) in donors was adjusted to achieve an arterial carbon dioxide tension ($PaCO_2$) of approximately 30 mm Hg. These ventilator settings were maintained for the remainder of the experiment.

Oxygen and carbon dioxide tension in blood and gas were measured with calibrated micro-Clark and Severinghaus electrodes (NOVA Biomedical Corporation) at 37° C. Blood pH was measured using a calibrated Sanz electrode (NOVA Biomedical Corporation) at 37° C. Blood gas tensions and pH were corrected to body temperature, pressure, saturated, using the algorithms of Thomas, L. J. 1972 (J. Appl. Physiol. 33:154–8). Oxygen consumption ($VO_2$) was calculated from the arterial and mixed venous oxygen content difference and cardiac output. Carbon dioxide elimination ($VCO_2$) was calculated from carbon dioxide tension in mixed-expired gas and expired minute ventilation, assuming carbon dioxide was not present in inspired gas. $VO_2$ and $VCO_2$ were indexed to body weight and converted to STPD.

Continuous ventilation:perfusion (VA/Q) distributions were estimated using the multiple inert gas elimination technique as described in Wagner, P D et al. 1974. (*J. Appl. Physiol.* 36:588–99) and Wagner P D et al. 1974 (*J. Appl. Physiol.* 36:600–5). The inert gases were extracted from blood by equilibration with nitrogen at 37° C. Inert gas concentrations in the gas phase were determined by gas chromatography, using megabore columns (DB1, J&W Scientific, Folsom, Calif.; Pora Plot U, Chrompack, Middleburg, The Netherlands) and a flame ionization and electron capture detector-equipped machine (Hewlett-Packard Co., Medical Products Group, Andover, Mass.)

A three hour period of left lung ischemia was initiated in 19 animals by occlusion of the left main pulmonary artery. EL-246, which recognizes both sheep L- and E-selectin, and DREG 56, which recognizes the lectin domain of human L-selectin, were infused into 8 and 3 animals, respectively, 10 minutes prior to reperfusion of the left lung. Each animal received a bolus infusion in 0.9% saline solution, intravenously, at a dose of 1 mg antibody/Kg body weight. Eight animals received no antibody treatment. Physiological parameters were recorded for all subjects at various time intervals for up to 6 hours following onset of reperfusion.

Figure 14:
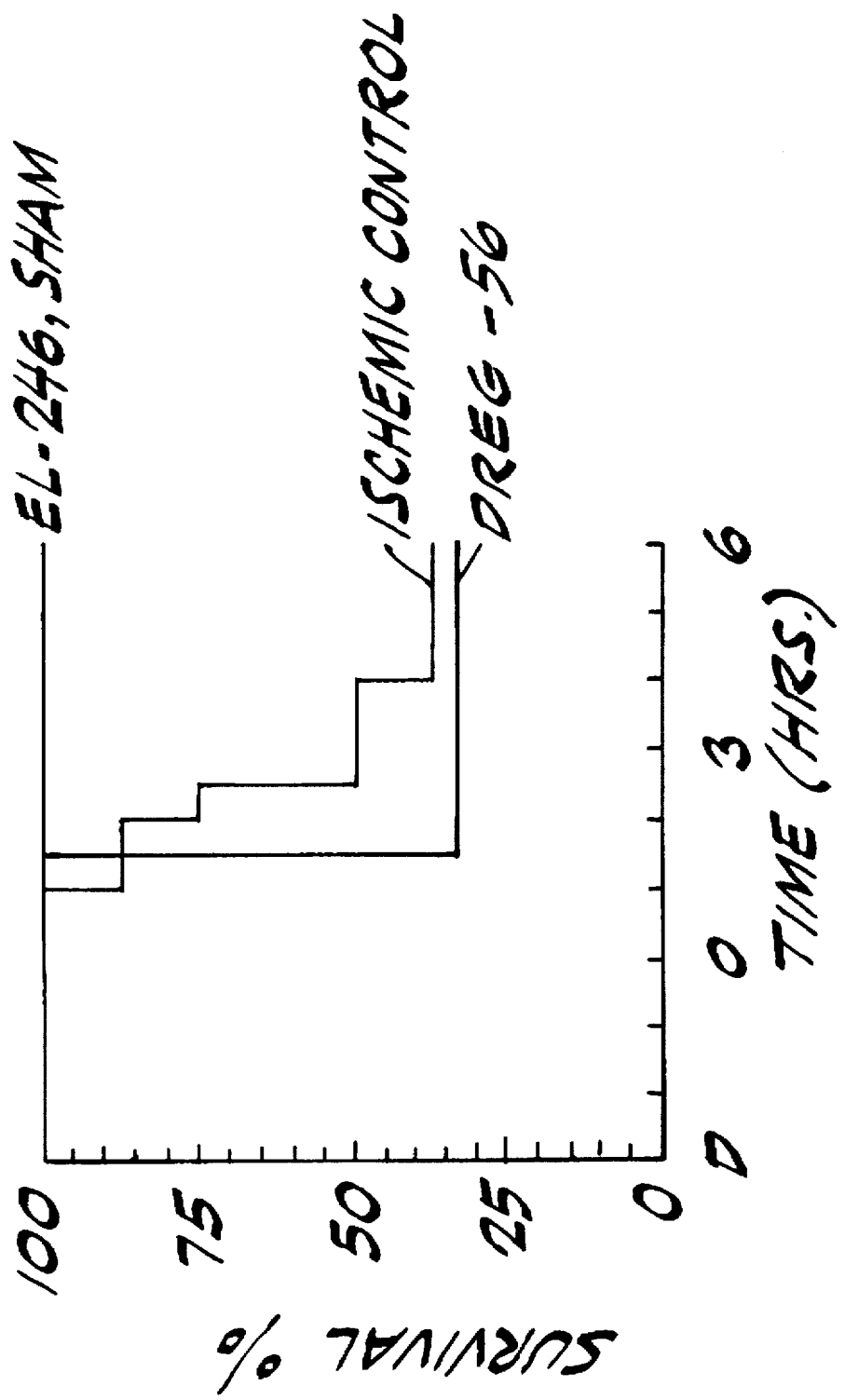
FIG. 14. EL-246 treatment of ewes prevents mortality caused by Ischemia/reperfusion injury in vivo. Ewes were treated with an anti-E/L-selectin (EL-246) monoclonal antibody, an anti-human L-selectin monoclonal antibody (DREG56), or received no treatment (ischemic control). The percent survival was plotted vs. time (hrs).

Five out of eight untreated animals (62.5% mortality) died within 6 hours as shown in FIG. 14. All of the untreated animals (ischemic controlled) showed a loss of lung function within 30 minutes following onset of reperfusion, which declined progressively throughout reperfusion. Loss of lung function was indicated by a decline in arterial oxygen tension ($P_aO_2$) with an increase in arterial carbon dioxide tension ($P_aCO_2$).

Two out of three DREG 56-treated animals (66.7% mortality) died within 6 hours as shown in FIG. 14. All of the DREG 56 treated animals showed a loss of lung function throughout the experiment. These results were not statistically different from the untreated controls. Therefore, DREG 56, which recognizes the lectin domain of L-selectin in humans and bovines, but does not recognize L-selectin in sheep, failed to protect sheep from ischemia/reperfusion injury.

All eight of the EL-246 treated animals (zero percent mortality) survived throughout the entire experiment (FIG. 14). All of the EL-246 treated animals demonstrated an immediate loss in lung function (within 30 minutes) following onset of reperfusion. However, within 2 hours the lung function in all EL-246 treated animals improved significantly to levels of $P_aO_2$ and $P_aCO_2$ found in the blood of normal animals. Therefore, EL-246 is an effective therapeutic in vivo as it resulted in 100% survival of treated animals, as well as improved lung function.

EXAMPLE 17

Determination of Saturating Levels of Antibody in the Serum of Treated Animals

Serum from treated animals (See Example 15) was tested 30 minutes after injection of EL-246 or DREG 56 for saturating levels of antibody. Staining of E-selection and L-selection cDNA transfected mouse L½ cells by flow cytometry was used for these analysis. Serial 2 fold dilutions of the serum samples were used to stain the transfectants, followed by FITC-second stage and the fluorescence compared to that given by saturating levels of purified EL-246 or DREG 56 antibody. Maximal staining of the transfectants was detected in all serum samples diluted 1:8 (both EL-246 and DREG 56) indicating that saturating levels of antibody were achieved in the animals.

EXAMPLE 18

½ life of EL-246 in circulation

Figure 15A:
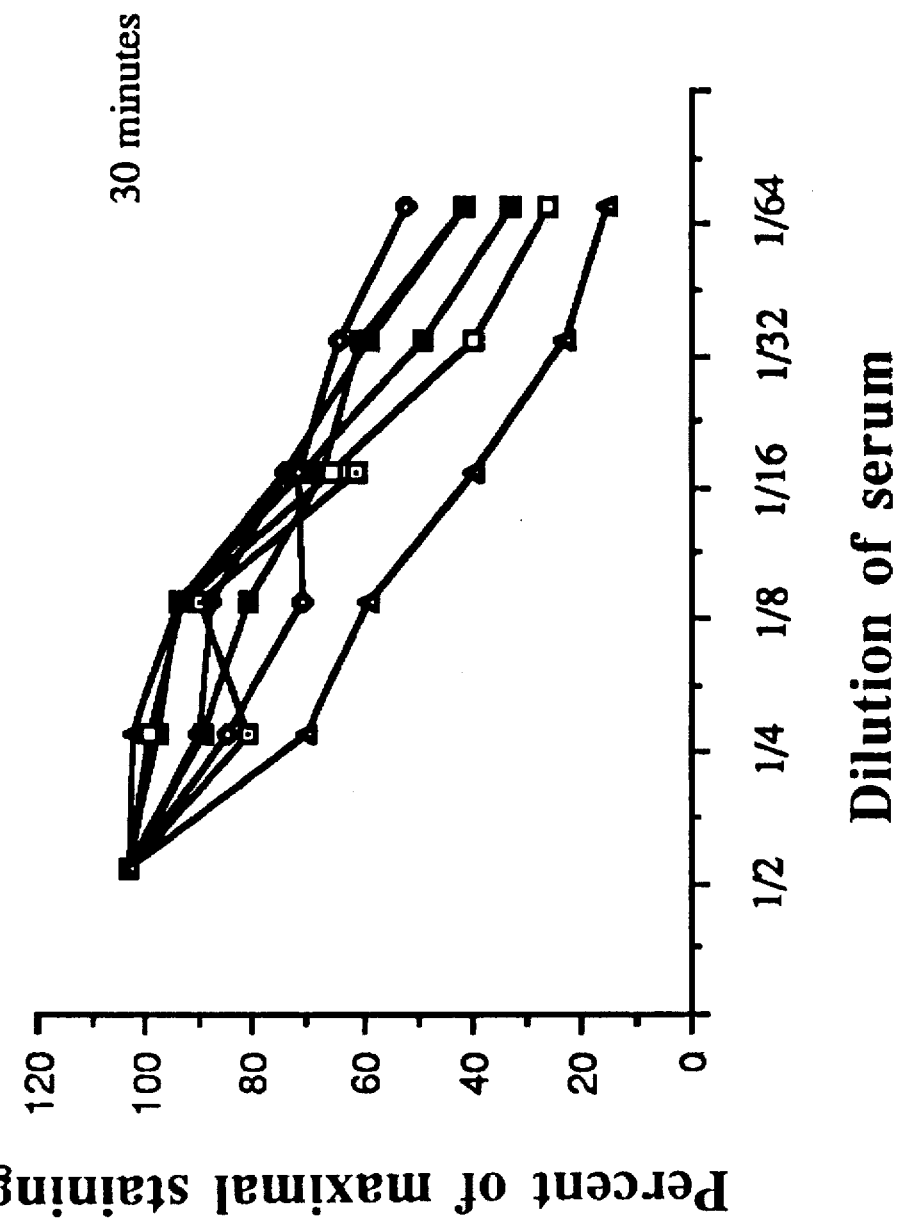
FIG. 15A, FIG. 15B, and FIG. 15C. Shows the percent of maximal fluorescence staining of L-selectin cDNA transfected mouse L½ cells treated with dilutions of serum samples taken at 30 (FIG. 15A), 90 (FIG. 15B) and 360 (FIG. 15C) minutes following onset of reperfusion in 8 animal treated with anti-E-/L-selectin monoclonal antibody (EL-246).
Figure 15B:
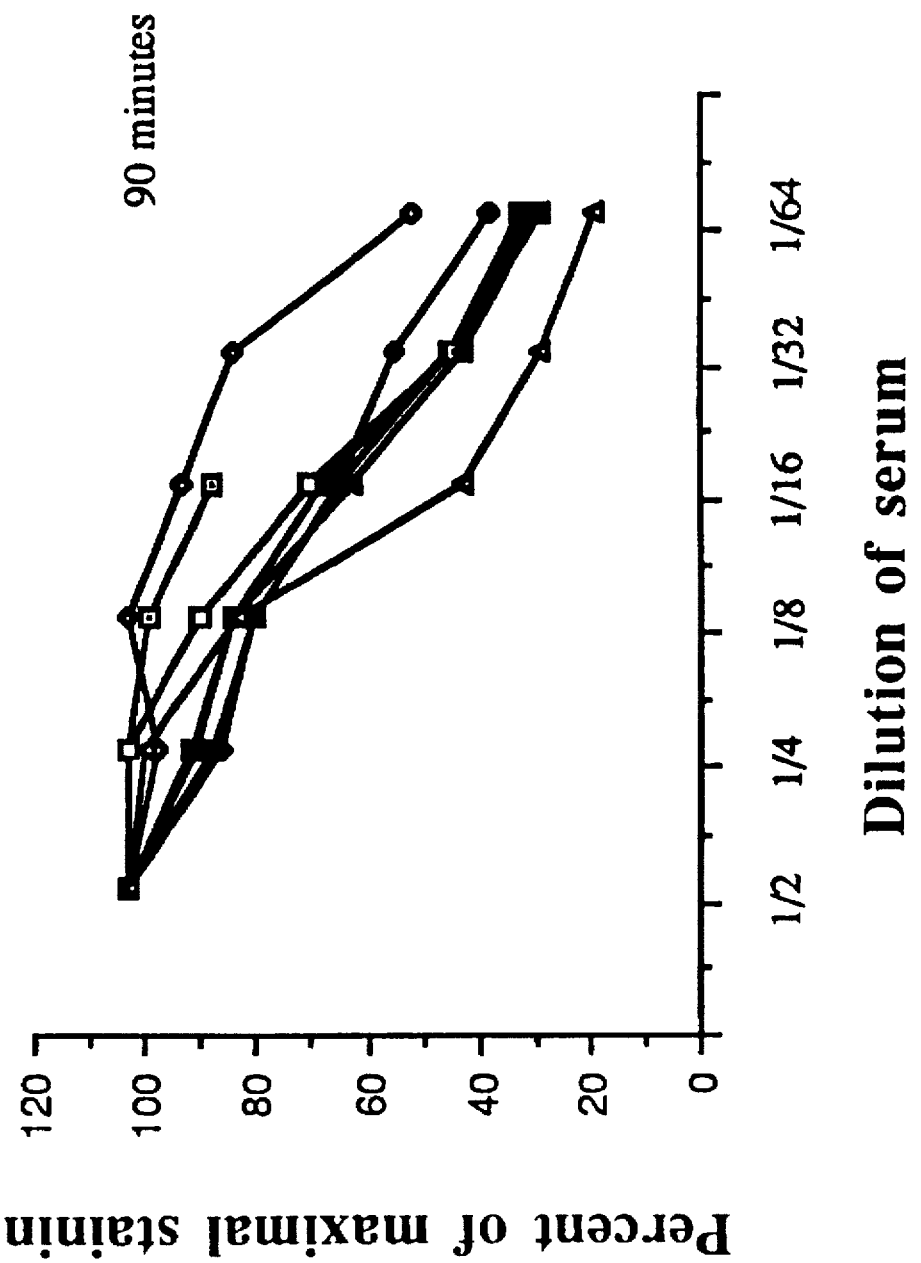
Figure 15C:
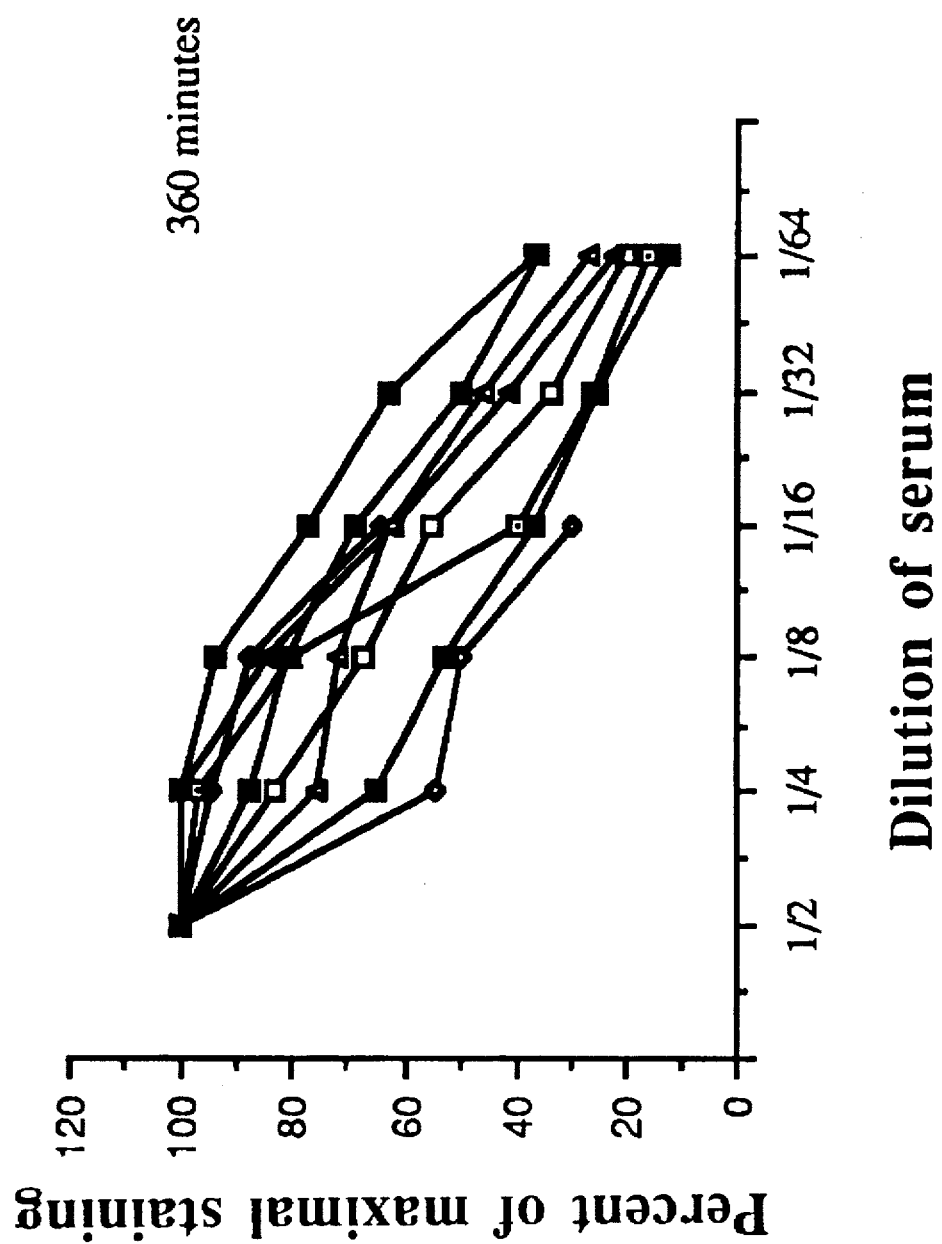

The titer of EL-246 in the serum of the eight treated animals was followed throughout the 6 hr experiment (Example 15). No significant drop in the level of EL-246 was noted. FIGS. 15A–C shows the percent of maximal staining of L-selectin transfectants treated with different dilutions of the serum samples taken from the eight animals at 30 (FIG. 15A), 90 (FIG. 15B), 360 (FIG. 15C) minutes following onset of reperfusion. Saturating levels of EL-246 following the injection of 1 mg/kg were maintained for 6 hrs, though variability in the titers at 6 hrs were noted (FIG. 15C). Thus EL-246 was not rapidly cleared from the circulation.

It is understood that the examples and embodiments described herein are for illustrative purposes only and that various modifications or changes in light thereof will be suggested to persons skilled in the art to be included within the spirit and purview of this application and scope of the appended claims.

I claim:

1. An isolated monoclonal antibody or antigen binding fragment thereof, which specifically binds a common antigenic determinant on E-selectin and L-selectin, said binding requires a short consensus repeat domain and said binding simultaneously or individually inhibits E-selectin and L-selectin functions.

2. The monoclonal antibody EL-246 secreted by a hybridoma having the ATCC Accession No. HB 11049 or antigen binding fragment thereof.

3. A cell line which secretes the monoclonal antibody according to claim 1.

4. The cell line having the ATCC Accession No. HB 11049 which secretes the monoclonal antibody according to claim 2.

5. The monoclonal antibody or antigen binding fragment according to claim 1, wherein the antibody or antigen binding fragment does not bind to P-selectin.

6. The monoclonal antibody or antigen binding fragment according to claim 1, wherein the antibody or antigen binding fragment selectively binds to L-selectin in humans, sheep, goats, cattle and pigs.

7. The monoclonal antibody or antigen binding fragment thereof according to claim 1 or 2 wherein the antibody or antigen binding fragment is further characterized by its ability to specifically inhibit leukocyte rolling on an endothelial cell layer.

8. The monoclonal antibody or antigen binding fragment thereof according to claim 1 or 2 wherein the antibody or antigen binding fragment is further characterized by its ability to specifically inhibit lymphocyte homing to peripheral tissues.

9. The monoclonal antibody or antigen binding fragment thereof according to claim 1 or 2 wherein the antibody or antigen binding fragment is further characterized by its ability to specifically inhibit an inflammatory response in humans, sheep, cattle and pigs.

10. A monoclonal antibody produced by a process comprising:
    (a) immunizing a mammal with an immunogen composed of cells stably expressing E-selectin, cells stably expressing L-selectin or a combination of cells stably expressing E-selectin and cells stably expressing L-selectin;
    (b) fusing lymphocytes from the immunized mammal with myeloma cells;
    (c) selecting hybrid cells that secrete antibodies wherein said antibodies have the characteristic of specifically binding a common antigenic determinant on L-selectin and E-selectin, said binding requires a short consensus repeat domain and said binding simultaneously or individually inhibits E-selectin and L-selectin mediated functions; and
    (d) isolating the antibodies.

11. The monoclonal antibody according to claim 10 wherein the immunogen is a human E-selectin cDNA transfected cell.

12. A pharmaceutical composition comprising the monoclonal antibody or antigen binding fragment according to claim 1, 2 or 10 and a pharmaceutically acceptable carrier.

13. The pharmaceutical composition according to claim 12 further comprising an anti-inflammatory agent selected from the group consisting of: catecholamines, resorcinols, salingenins, ephedrine, glucocorticoids, cromolyn sodium, and anticholinergics.

14. A process for producing monoclonal antibodies which specifically bind to a common antigenic determinant on E-selectin and L-selectin comprising:
    (a) immunizing a mammal with an immunogen composed of cells stably expressing E-selectin, cells stably expressing L-selectin or a combination of cells stably expressing E-selectin and cells stably expressing L-selectin;
    (b) fusing lymphocytes from the immunized mammal with myeloma cells;
    (c) selecting hybrid cells that secrete antibodies wherein said antibodies have the characteristic of specifically binding a common antigenic determinant on L-selectin and E-selectin, said binding requires a short consensus repeat domain and said binding simultaneously or individually inhibits E-selectin and L-selectin mediated functions; and
    (d) isolating the antibodies.

15. The method according to claim 14 wherein immunogen is a human E-selectin cDNA transfected cell.

16. A method of inhibiting the adhesion of a first cell bearing an E-selectin molecule to a second cell bearing an L-selectin molecule comprising:
    contacting said cells with the antibodies or antigen binding fragments of claim 1 under conditions wherein the antibodies bind to the cells in an amount sufficient to prevent the first cell from binding to the second cell.

17. The method according to claim 16, in which the monoclonal antibody is EL-246 secreted by a hybridoma having the ATCC Accession No. HB 11049.

18. The method according to claim 16 wherein the E-selectin and L-selectin bearing cells are at a site of inflammation in a mammal.

19. A method of detecting E-selectin and L-selectin bearing cells in biological sample suspected of containing the selectin bearing cells comprising:
    a. contacting the sample with the antibodies or antigen-binding fragments of claim 1 or 2 to form an immune complex with the E-selectin and L-selectin bearing cells, and;
    b. detecting the presence of the immune complex.

20. A method of treating a mammal to inhibit tissue damage occurring at an inflammatory site in any part of the body of a mammal experiencing a leukocyte-mediated inflammatory condition, said method comprising:
    administering in vivo a monoclonal antibody according to claim 1 or 2 in an amount sufficient to bind specifically to L-selectin and E-selectin molecules expressed on the surface of leukocytes and endothelial cells, respectively, and sufficient to inhibit tissue damage.

21. The method according to claim 20 in which said inflammatory site is located at the vascular endothelial cell interface or subcellular matrix of a body part.

22. The method according to claim 20 in which said inflammatory site involves endothelial tissue of a body part.

23. The method according to claim 20 in which said inflammatory site is in a joint or body part.

24. The method according to claim 20 in which said inflammatory site is the result of a myocardial infarct.

25. The method according to claim 20 in which the monoclonal antibody is administered intravenously at a selected time period prior to or during said inflammatory condition.

26. The method according to claim 20 in which said monoclonal antibody binds to L-selectin and E-selectin expressing cells and does not bind to P-selectin.

27. A method of inhibiting an inflammatory response at a site of ischemia-reperfusion injury in a mammal, said method comprising:

administration of an effective amount of a monoclonal antibody or antigen binding fragment thereof according to claim 1 or 2, said amount inhibits the inflammatory response at the site of ischemia-reperfusion injury.

28. The method according to claim 27, wherein the site is selected from the group consisting of a heart, lung, joint, brain, limb, blood vessel, lymph node, spleen, crush injury site, spinal cord or transplantation site.

29. The method according to claim 27 wherein the ischemic injury is caused by a myocardial infarction, shock, stroke, organ transplantation, crush injury, limb replantation, frostbite or lung ischemia/reperfusion injury.

30. The method according to claim 27 said amount is effective to inhibit loss of lung function.

31. The method according to claim 27 wherein the monoclonal antibody is EL-246 which is secreted by a cell line having the ATCC Accession No. HB 11049.

32. A method to inhibit leukocyte rolling on an endothelial cell layer comprising:

treatment of the leukocytes or the endothelial cell layer with an amount of the monoclonal antibody or antigen binding fragment according to claim 1 or 2, said amount is effective to inhibit leukocyte rolling.

33. The method according to claim 32 wherein the endothelial cell layer is an endothelium lining a lymphatic vessel, artery, vein or postcapillary venules.

34. A method to inhibit lymphocyte homing to peripheral tissue of a mammal comprising: administration of an effective amount of the monoclonal antibody or antigen binding fragment according to claim 1 or 2, said amount inhibits the homing of lymphocytes from the blood to the peripheral tissue.

* * * * *